US007048929B1

(12) United States Patent
Sodroski et al.

(10) Patent No.: US 7,048,929 B1
(45) Date of Patent: May 23, 2006

(54) STABILIZED PRIMATE LENTIVIRUS ENVELOPE GLYCOPROTEINS

(75) Inventors: Joseph G Sodroski, Medford, MA (US); Richard T. Wyatt, Andover, MA (US); Peter D. Kwong, New York, NY (US); Wayne A. Hendrickson, New York, NY (US); Michael Farzan, Brookline, MA (US)

(73) Assignees: Dana-Farber Cancer Institute, Inc., Boston, MA (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/446,820

(22) PCT Filed: Nov. 10, 1998

(86) PCT No.: PCT/US98/24001

§ 371 (c)(1),
(2), (4) Date: Apr. 30, 2001

(87) PCT Pub. No.: WO99/24465

PCT Pub. Date: May 20, 1999

Related U.S. Application Data

(63) Continuation-in-part of application No. 09/100,762, filed on Jun. 18, 1998, now abandoned, and a continuation-in-part of application No. 09/100,631, filed on Jun. 18, 1998, now abandoned, and a continuation-in-part of application No. 09/100,521, filed on Jun. 18, 1998, now abandoned, and a continuation-in-part of application No. 09/100,763, filed on Jun. 18, 1998, now abandoned, and a continuation-in-part of application No. 09/100,529, filed on Jun. 18, 1998, now abandoned, and a continuation-in-part of application No. 09/100,764, filed on Jun. 18, 1998, now abandoned, and a continuation-in-part of application No. 08/976,741, filed on Nov. 24, 1997, now abandoned, and a continuation-in-part of application No. 08/967,403, filed on Nov. 10, 1997, now abandoned, and a continuation-in-part of application No. 08/966,932, filed on Nov. 10, 1997, now abandoned, and a continuation-in-part of application No. 08/967,148, filed on Nov. 10, 1997, now abandoned, and a continuation-in-part of application No. 08/967,708, filed on Nov. 10, 1997, now abandoned, and a continuation-in-part of application No. 08/966,987, filed on Nov. 10, 1997, now abandoned.

(60) Provisional application No. 60/089,581, filed on Jun. 17, 1998, provisional application No. 60/089,580, filed on Jun. 17, 1998.

(51) Int. Cl.
*A61K 39/21* (2006.01)

(52) U.S. Cl. .................. 424/188.1; 424/208.1
(58) Field of Classification Search ............. 424/188.1, 424/208.1
See application file for complete search history.

(56) References Cited

U.S. PATENT DOCUMENTS 5,817,316 A   10/1998   Sodroski et al.

OTHER PUBLICATIONS

Freed, E. O., et al., 1991, "Identification of the principle neutralizing determinant of human immunodeficiency virus type 1 as a fusion domain.", J. Virol. 65(1):190-194.*

McKeating, J. A., et al., 1992, "Amino acid residues of the human immunodeficiency virus type 1 gp120 critical for the binding of rat and human neutralizing antibodies that block that gp120-sCD4 interaction.", Virol. 190:134-142.*

Thali, M., et al., 1993, "Characterization of conserved human immunodeficiency virus type 1 and gp120 neutralization epitopes exposed upon gp120-CD4 binding.", J. Virol. 67(7):3978-3988.*

Sullivan, N., et al., 1993, "Effect of amino acid changes in the V1/V2 region of the human immunodeficiency virus type 1 gp120 glycoprotein on subunit association, syncytium formation, and recognition by a neutralizing antibody.", J. Virol. 67(6):3674-3679.*

Cao, J., et al., 1993, "Effects of amino acid changes in the extracellular domain of the human immunodeficiency virus type 1 gp41 envelope glycoprotein.", J. Virol. 67(5):2747-2755.*

(Continued)

*Primary Examiner*—Jeffrey S. Parkin
(74) *Attorney, Agent, or Firm*—Nixon Peabody LLP

(57) ABSTRACT

A modified polypeptide corresponding to an envelope glycoprotein of a primate lentivirus is described. The polypeptide has been modified from the wild-type structure so that it has cysteine amino acid residues introduced to create disulfide bonds, a cavity is filled with hydrophobic amino acids, a Proresidue is introduced at a defined turn structure of the protein, or the hydrophobicity is increased across the interface between different domains, while retaining the overall 3-dimensional structure of a discontinuous conserved epitope of the wild-type protein. Preferably, the polypeptide has more than one of those characteristics. Preferably, the primate lentivirus is HIV, and the protein is HIV-1 gp120.

15 Claims, 9 Drawing Sheets

OTHER PUBLICATIONS

Alkhatib, G., et al., *Science* 272:1955-1958 (1996).
Allan, JS., et al., *Science* 228:1091-1093 (1985).
Altschul, SF., et al., *Nucleic Acids Res.* 25: 3389-3402 (1997).
Arendrup, et al., *J. AIDS* 5:303-307 (1992).
Arthos, J., et al., *Cell* 57:469 (1989).
Baggioline, M., et al., *Adv. Immunol.* 55:97-179 (1994).
Barre-Sinousi, F., et al., *Science* 220:868-871 (1983).
Berkower, et al., *J. Exp. Med.* 170:1681-1695 (1989).
Berman, PW., et al., *Nature* 345:622-625 (1990).
Binley, J., et al., *AIDS Res. Hum. Retroviruses,* 14:191-198 (1997).
Bolmstedt, A., et al., *J. AIDS* 12:213-220 (1996).
Brodsky, MH., et al., *J Immunol.* 144:3078-3086 (1990).
Bruck, et al., *Vaccine* 12:1141-1148 (1994).
Bullough, P., et al., *Nature* 371:37-43 (1994).
Burton, et al., *Science* 266:1024-1027 (1994).
Cao, J., et al., *J. Virol.* 71:9808-9812 (1997).
Carr, CM., et al., *Cell* 73:823-832 (1993).
Chan, DC., et al., *Cell* 89:263-273 (1997).
Chen, CH., et al., *J. Virol.* 69:3771-3777 (1995).
Chen, Z., et al., *J. Virol.* 71:2705-2714 (1997).
Cheng-Mayer, C., et al., *Science* 240:80-82 (1988).
Choe, H., et al., *Cell* 85:1135-1148 (1996).
Clark, SJ, et al., *N. Engl. J. Med.* 324:950-960 (1991).
Cocchi, F., et al., *Nature Med.* 2:1244-1247 (1996).
Cocchi, F., et al., *Science* 270:1811-1815 (1995).
Connor, R., et al., *J. Exp. Med.* 185:628 (1997).
Connor, RI., et al., *J. Virol.* 67:1772-1778 (1993).
Coombs, RW., et al., *N. Engl. J. Med.* 321:1626-1631 (1989).
Cordonnier, A., et al., *Nature* 340:571-574 (1989).
D'Souza, et al., *J. Infect. Dis.* 175: 1056-1062 (1997).
Daar, ES., et al., *N. Engl. J. Med.* 324:961-964 (1991).
Daar, et al., *Proc. Natl. Acad. Sci. USA* 87:6574-6578 (1990).
Dalgleish, AG., et al., *Nature* 312:763-767 (1984).
Dalum, et al., *Mol. Immunol.* 34:1113-1120 (1997).
Davidson, et al., *Nat. Genet* 3:219 (1993).
Dean, M., et al., *Science* 273:1856-1862 (1996).
Dempsey, P., et al., *Science* 271:348-350 (1996).
Deng, HK., et al., *Nature* 381:661-666 (1996).
Doranz, BJ., et al., *Cell* 85:1149-1158 (1996).
Dragic, T., et al., *Nature* 381:667-673 (1996).
Earl, PL., et al., *J. Virol.* 65:2047-2055 (1991).
Earl, PL., et al., *Proc. Natl. Acad. Sci. USA* 87:648-652 (1990).
Emini, et al., *Nature* 355:728-730 (1991).
Fauci, AS., et al., *Ann. Inter. Med.* 124:654-663 (1996).
Feng, Y., et al., *Science* 272:872-877 (1996).
Fenyo, E., et al., *J. Virol.* 62:4414-4419 (1988).
Freed, E., et al., *Proc. Natl. Acad. Sci. USA* 87:4650-4654 (1990).
Fung, et al., *J. Virol.* 66:848-856 (1992).
Gallo, RC., et al., *Science* 224:500-503 (1984).
Gegerfelt, et al., *Virology* 185:162-168 (1991).
Geller, AI., et al., *J. Neurochem* 64:487 (1995).
Geller, AI., et al., *Proc Natl. Acad. Sci. U.S.A.* 87:1149 (1990).
Geller, AI., et al., *Proc Natl. Acad. Sci. U.S.A.* 90:7603 (1993).
Gerard, N., et al., *Curr. Opin. Immunol.* 6:140-145 (1994).
Girard, et al., *Proc. Natl. Acad. Sci. USA* 88:542-546 (1991).
Gorny, et al., *J. Virol.* 66:7538-7542 (1992).
Haigwood, et al., *AIDS Res. Hum. Retro.* 6:855-869 (1990).
Haigwood, et al., *J. Virol.* 66:172-182 (1992).
Ho, DD., et al., *N. Engl. J. Med.* 321:1621-1625 (1989).
Ho, et al., *J. Virol.* 65:489-493 (1991).
Javaherian, et al., *Science* 250:1590-1593 (1990).
Kang, et al., *Proc. Natl. Acad. Sci. USA* 88:6171-6175 (1991).
Kaplitt, MG., et al., *Nat. Genet.* 8:148 (1994).
Karlsson, G., et al., *J. Virol.* 71:4218 (1997).
Klaniecki, et al., *AIDS Res. Hum. Retro.* 7:791-798 (1991).
Klatzmann, D., et al., *Nature London* 312:767-68 (1984).
Kowalski, M., et al., *Science* 237:1351-1355 (1987).
Lasky, L., et al., *Cell* 50:975-985 (1987).
LeGal LaSalle, et al., *Science* 259: 988 (1993).
Leonard, CK., et al., *J. Biol. Chem.* 265:10373-10382 (1990).
Liu, R., et al., *Cell* 86:367-378 (1996).
Lu, M., et al., *Nature Structural Biol.* 2:1075-1082 (1995).
Marcon, L., et al., *J. Virol.* 71:2522-2527 (1997).
Matthews, et al., *Proc. Nat. Acad. Sci. USA* 83:9709-9713 (1986).
McKeating, et al., *J. Virol.* 67:4932-4944 (1993).
McKeating, et al., *Virology* 190:134-142 (1992).
Moebius, U., et al., *J. Exp. Med.* 176:507-517 (1982).
Moore, et al., *J. Virol.* 69:101-109 (1995).
Moore, et al., *J. Virol.* 67:6136-6151 (1993).
Moore, et al., *J. Virol.* 67:863-875 (1993).
Moore, et al., *J. Virol.* 69:122-133 (1995).
Moore, et al., *J. Virol.* 70:1863-1872 (1996).
Moore, J., et al., *J. Virol.* 68:469-484 (1994).
Moore, J., et al., *J. Virol.* 68:8350-8364 (1994).
Muster, et al., *J. Virol.* 67:6642-6647 (1993).
Myers, G., et al., "Human Retroviruses and AIDS: A Compilation and Analysis of Nucleic Acid and Amino Acid Sequences," *Los Alamos National Laboratory,* (1994).
Nara, et al., *J. Virol.* 64:3779-3791 (1990).
Ohno, et al., *Proc. Natl. Acad. Sci. USA* 88:10726-10729 (1991).
Olshevsky, U., et al., *J. Virol.* 64:5701-5707 (1990).
Peterson, A., et al., *Cell* 54:65-72 (1988).
Pinter, A., et al., *J. Virol.* 63:2674-2679.
Pollard, S., et al., *EMBO J.* 11:585-591 (1992).
Posner, et al., *J. Immunol.* 16:4325-4332 (1991).
Premack, BA., et al., *Nature Medicine* 11:1174-1178 (1996).
Profy, et al., *J. Immunol.* 144:4641-4647 (1990).
Roben, P., et al., *J. Virol.* 68:4821-4828 (1994).
Robey, W., et al., *Proc. Natl. Acad. Sci. USA* 83:7023-7027 (1986).
Robey, WG., et al., *Science* 228:593-595 (1985).
Robinson, J., et al., *AIDS Res. Hum. Retro* 6:567-580 (1990).
Rusche, et al., *Proc. Natl. Acad. Sci. USA* 84:6924-6928 (1987).
Rusche, J., et al., *Proc. Natl. Acad. Sci. USA* 85:3198-3202 (1988).
Ryu, SE., et al., *Nature London* 348:419-425 (1990).
Samson, M., et al., *Nature* 382:722-725 (1996).
Sattentau, Q., et al., *J. Exp. Med.* 174:407-415 (1991).
Sattentau, Q., et al., *J. Virol.* 67:7388-7393 (1993).
Sawyer, et al., *J. Virol.* 67:1342-1349 (1994).
Schuitemaker, H., et al., *J. Virol.* 66:1354-1360 (1991).
Speck, R., et al., *J. Virol.* 71:7136-7139 (1997).
Starcich, BR., et al., *Cell* 45:637-648 (1986).
Steimer, BR., et al., *Science* 254:105-108 (1991).
Sullivan, et al., *J. Virol.* 69:4413-4422 (1995).
Thali, et al., *J. Virol.* 65:6188-6193 (1991).

Thali, et al., *J. Virol.* 66:5635-5641 (1992).
Thali, M., et al., *J. Virol.* 67:3978-3988 (1993).
Tilley, et al., *Res. Virol.* 142:247-259 (1991).
Trkola, A., et al., *J. Virol.* 70:1100-1108 (1996).
Trkola, A., et al., *Nature* 384: 184-187 (1996).
Wang, J., et al., *Nature London* 348:411-418 (1990).
Watkins, B., et al., *J. Virol.* 67:7493 (1993).
Weissenhorn, W., et al., *EMBO J.* 15:1507-1514 (1996).
Weissenhorn, W., et al., *Nature* 387:426-430 (1997).
Wu, L., et al., *Nature* 384:179-183 (1996).
Wyatt, et al., *J. Virol.* 69:5723-5733 (1995).
Wyatt, R., et al., *J. Virol.* 67:4557-4565 (1993).
Wyatt, R., et al., *J. Virol.* 71:9722-9731 (1997).
Yang, et al., *J. Virol.* 69:2004 (1995).
Zhang, L., et al., *Nature* 383:768 (1996).
Zhu, T., et al., *Science* 261:1179-1181 (1993).

\* cited by examiner

STABILIZED PRIMATE LENTIVIRUS ENVELOPE GLYCOPROTEINS

This application is a national stage entry under 35 U.S.C. § 371 of international application PCT/US98/24001, filed Nov. 10, 1998, which claims benefit under 35 U.S.C. § 120 as a continuation-in-part of the following U.S. applications: U.S. Ser. No. 08/966,932, filed Nov. 10, 1997, now abandoned; U.S. Ser. No. 08/967,148, fled Nov. 10, 1997, now abandoned; U.S. Ser. No. 08/967,708, filed Nov. 10, 1997, now abandoned; U.S. Ser. No. 08/967,403, filed Nov. 10, 1997, now abandoned; U.S. Ser. No. 08/966,987, filed Nov. 10, 1997, now abandoned; U.S. Ser. No. 08/976,741, filed Nov. 24, 1997, now abandoned; U.S. Ser. No. 09/100,762, filed Jun. 18, 1998, now abandoned; U.S. Ser. No. 09/100,631, filed Jun. 18, 1998, now abandoned; U.S. Ser. No. 09/100,521, filed Jun. 18, 1998, now abandoned; U.S. Ser. No. 09/100,763, fled Jun. 18, 1998, now abandoned; U.S. Ser. No. 09/100,529, filed Jun. 18, 1998, now abandoned; and U.S. Ser. No. 09/100,764, filed Jun. 18, 1998, now abandoned; and which claimed benefit under 35 U.S.C. § 119(e) of U.S. provisional application 60/089,581, filed Jun. 17, 1998, now abandoned, and U.S. provisional application 60/089,580, filed Jun. 17, 1998, now abandoned.

FIELD OF THE INVENTION

The present invention is directed to envelope polypeptides having a structure that approximates conformational discontinuous epitopes of a primate lentivirus envelope protein, but as a result of modifications of that structure has enhanced stability, raises a greater range of antibodies to conserved epitopes, and/or has enhanced immunogenicity for broadly neutralizing epitopes.

BACKGROUND OF THE INVENTION

Human immunodeficiency virus type 1 (HIV-1) is the cause of acquired immunodeficiency syndrome (AIDS), which is characterized by the depletion of CD4-positive lymphocytes (See, Barre-Sinoussi, F., et al., "Isolation of a T-lymphotropic Retrovirus From a Patient at Risk for Acquired Immunodeficiency Syndrome (AIDS)," *Science* 220:868–871 (1983); Gallo, R C, et al., "Frequent Detection and Isolation of Cytopathic Retroviruses (HTLV-III) From Patients with AIDS and at Risk for AIDS," *Science* 224: 500–503 (1984)). Infection of humans by HIV-1 typically involves an initial period of acute, high-level viremia, followed by a chronic, low-level viremia (See, Coombs, R W, et al., "Plasma Viremia in Human Immunodeficiency Virus Infection," *N. Engl. J. Med.* 321:1626–1631 (1989); Clark, S J, et al., "High titers of Cytopathic Virus in Plasma from Patients with Symptomatic Primary HIV-1 Infection," *N. Engl. J. Med.* 324:950–960 (1991); Daar, E S, et al., "Transient High Levels of Viremia in Patients with Primary immunodeficiency Virus Type 1 Infection," *N. Engl. J. Med.* 324:961–964 (1991); Fauci, A S, et al., "Immunopathogenic Mechanisms of HIV Infection," *Ann. Inter. Med.* 124:654–663 (1996)). It is thought that the antiviral immune response helps to determine the "set-point" for chronic viremia. HIV-1 persistence results in progressive CD4-positive lymphocyte decline, which ultimately compromises the immune response, including that directed against HIV-1. The resulting resurgence of high-level viremia is a harbinger of poor clinical outcome (See, Ho, DD, et al., "Quantitation of Human Immunodeficiency Virus Type 1 in the Blood of Infected Persons," *N. Engl. J. Med.* 321:1621–1625 (1989)).

The envelope protein of a lentivirus is the most visible portion of the virion because it is on the surface of the virus particle. Thus, considerable attention has focussed on the envelope protein as a target for inhibiting viral entry. Strategies that have been used include using the envelope protein to generate an immune response, decoys for the envelope protein, etc. These approaches have not yet been successful.

It was recently reported that a large scale clinical trial was going to be attempted with an HIV envelope protein as an immunogen. While the initial trials with the protein have not been reported to be promising in terms of showing any significant protective immunity, they have also not indicated any significant harm caused by the vaccine candidate. The fact that a clinical trial with this type of preliminary results would be attempted shows the importance placed upon the use of the envelope protein and underscores the need for improvements in enhancing the immunogenicity of the envelope protein.

The envelope protein is an attractive target because, like that of other retroviruses, the entry of HIV-1 into target cells is mediated by the viral envelope glycoproteins, gp120 and gp41, which are derived from a gp160 precursor (See, Allan, J S, et al., "Major Glycoprotein Antigens That Induce Antibodies in AIDS Patients are Encoded by HTLV-III," *Science* 228:1091–1093 (1985); Robey, W G., et al., "Characterization of Envelope and Core Structural Gene Products of HTLV-III with Sera from AIDS Patients," *Science* 228: 593–595 (1985)). The gp160 glycoprotein is created by the addition of N-linked, high mannose sugar chains to the approximately 845–870 amino acid primary translation product of the env gene in the rough endoplasmic reticulum. Trimerization of gp160 in the endoplasmic reticulum is mediated by the formation of a coiled coil within the gp41 ectodomainu. (See, Earl, P L., et al., "Oligomeric Structure of the Human Immunodeficiency Virus Type 1 Envelope Glycoprotein," *Proc. Natl. Acad. Sci. USA* 87:648–652 (1990); Pinter, A., et al., "Oligomeric Structure of gp41, the Transmembrane Protein of Human Immunodeficiency Virus Type 1," *J. Virol.* 63:2674–2679; Lu, M., et al., "A Trimeric Structural Domain of the HIV-1 Transmembrane Glycoprotein," *Nature Structural Biol.* 2:1075–1082 (1995); Chan, D C, et al., "Core Structure of gp41 from the HIV Envelope Glycoprotein," *Cell* 89:263–273 (1997); and Weissenhorn, W., et al., "Atomic Structure of the Ectodomain from HIV-1 gp41," *Nature* 387:426–430 (1997)). The gp160 trimers are transported to the Golgi apparatus, where cleavage by a cellular protease generates the mature gp120 and gp41 glycoproteins, which remain associated through non-covalent interactions (Earl, P L, et al., "Folding, Interaction with GRP78-BiP, Assembly and Transport of the Human Immunodeficiency Virus Type 1 Envelope Protein," *J. Virol.* 65:2047–2055 (1991); and Kowalski, M., et al., "Functional Regions of the Envelope Glycoprotein of Human Immunodeficiency Virus Type 1," *Science* 237:1351–1355 (1987)). In mammalian host cells, addition of complex sugars to selected, probably surface-exposed, carbohydrate side chains of the envelope glycoproteins occurs in the Golgi apparatus. (See, Leonard, C K, et al., "Assignment of Intrachain Disulfide Bonds and Characterization of Potential glycosylation Sites of the Type 1 Recombinant Human Immunodeficiency Virus Envelope Glycoprotein (gp120) Expressed in Chinese Hamster Ovary Cells," *J. Biol. Chem.* 265:10373–10382 (19990)).

Most of the surface-exposed elements of the oligomeric envelope glycoprotein complex are contained on the gp120 exterior envelope glycoprotein. (See, Moore, J., et al., "Probing the Structure of the Human Immunodeficiency Virus Surface Glycoprotein gp120 with a Panel of Monoclonal Antibodies," *J. Virol.* 68:469–484 (1994)). When the gp120 glycoproteins derived from different primate immunodeficiency viruses are compared, five conserved regions (C1 to C5) and five variable regions (V1 to V5) can be identified. (See, Starcich, B R, et al., "Identification and Characterization of Conserved and Variable Regions of the Envelope Gene HTLV-III/LAV, the Retrovirus of AIDS," *Cell* 45:637–648 (1986); Myers, G., et al. "Human Retroviruses and AIDS: A Compilation and Analysis of Nucleic Acid and Amino Acid Sequences," *Los Alamos National Laboratory*, (1994)). Intramolecular disulfide bonds in the gp120 glycoprotein result in the incorporation of the first four variable regions into large, loop-like structures. Antibody binding studies and deletion mutagenesis have indicated that the major variable loops are well-exposed on the surface of the gp120 glycoprotein. (See, Wyatt, R., et al., "Functional and Immunologic Characterization of Human Immunodeficiency Virus Type 1 Envelope Glycoproteins Containing Deletions of the Major Variable Regions," *J. Virol.* 67:4557–4565 (1993); Pollard, S., et al., "Truncated Variants of gp120 bind CD4 with High Affinity and Suggest a Minimum CD4 Binding Region," *EMBO J.* 11:585–591 (1992)).

The mature envelope glycoprotein complex is incorporated into HIV-1 virions, where it mediates virus entry into the host cell. The gp120 exterior glycoprotein binds the CD4 glycoprotein, which serves as the primary receptor. (See, Klatzmann, D., et al., "T-lymphocyte T4 Molecule Behaves as the Receptor for Human Retrovirus LAV," *Nature London* 312:767–768 (1984); and Dalgleish, A G., et al., "The CD4 (T4) Antigen is an Essential Component of the Receptor for the AIDS Retrovirus," *Nature* 312: 763–767 (1984)). The association of gp120 with CD4 is mediated by the interaction of a discontinuous gp120 structure with the CDR2-like region of the CD4 amino-terminal domain. (See, Brodsky, M H., et al., "Analysis of the Site in CD4 that Binds to the HIV Envelope Glycoprotein," *J. Immunol.* 144: 3078–3086 (1990); Peterson, A., et al., "Genetic analysis of Monoclonal Antibody and HIV binding Sites on the Human Lymphocyte Antigen CD4," *Cell* 54:65–72 (1988); Moebius, U., et al., "The Human Immunodeficiency Virus gp120 Binding Site on CD4: Delineation by quantitative Equilibrium and Kinetic Binding Studies of Mutants in Conjunction with a High-Resolution CD4 Atomic Structure," *J. Exp. Med.* 176: 507–517 (1982); Arthos, J., et al., "Identification of the Residues in Human CD4 Critical for the binding of HIV," *Cell* 57:469 (1989); Ryu S E., et al., "Crystal Structure of an HIV-binding Recombinant Fragment of Human CD4," *Nature London* 348:419–425 (1990); and Wang, J., et al., "Atomic Structure of a Fragment of Human CD4 containing Two immunoglobulin-like Domains," *Nature London* 348: 411–418 (1990)). Amino acids in the gp120 C3 and C4 regions have been implicated in CD4 binding. (See, Cordonnier, A., et al., "Single Amino Acid Changes in HIV Envelope Affect Viral Tropism and Receptor Binding, *Nature* 340:571–574 (1989); Lasky, L., et al., "Delineation of a Region of the Human Immunodeficiency Virus Type 1 gp120 Glycoprotein Critical for Interaction with the CD4 Receptor," *Cell* 50:975–985 (1987); and Olshevsky, U., et al., "Identification of Individual HIV-1 gp120 Amino Acids Important for CD4 Receptor Binding," *J. Virol.* 64:5701–5707 (1990)). The association of gp120 with CD4 is believed to initiate conformational changes in the HIV-1 envelope glycoprotein complex, leading to interactions with members of the chemokine receptor family. (See, Sattentau, Q., et al., "Conformational Changes Induced in the Human Immunodeficiency Virus Envelope Glycoprotein by Soluble CD4 binding," *J. Exp. Med.* 174:407–415 (1991); Thali, M., et al., "Characterization of Conserved Human Immunodeficiency Virus Type 1 (HIV-1) gp120 neutralization Epitopes Exposed Upon gp120-CD4 Binding," *J Virol* 67:3978–3988 (1993); Sattentau, Q., et al., "Conformational Changes Induced in the Envelope Glycoproteins of Human and Simian Immunodeficiency Virus by Soluble Receptor Binding," *J. Virol.* 67:7388–7393 (1993); Trkola, A., et al., "CD4-dependent, antibody-sensitive Interactions Between HIV-1 and its Co-receptor CCR05," *Nature* 384:184–187 (1996); and WU, L., et al., "CD4-induced Interaction of Primary HIV-1 gp120 Glycoproteins with the Chemokine Receptor CCR5," *Nature* 384:179–183 (1996).

Chemokine receptors are G protein-coupled, seven-membrane-spanning proteins involved in leukocyte chemotaxis. (See, Baggioline, M., et al., "Interleukin-8 and Related Chemotactic Cytokines-CXC and CC Chemokines," *Adv. Immunol.* 55:97–179 (1994); Gerard, N., et al., "the Pro-Inflammatory Seven-Transmembrane-Segment Receptors of the Leukocyte," *Curr. Opin. Immunol.* 6:140–145 (1994); and Premack, B A., et al, "Chemokine Receptors: Gateways to Inflammation and Infection," *Nature Medicine* 11:1174–1178 (1996)). Most laboratory-adapted HIV-1 viruses utilize a CXC chemokine receptor called CXCR4 (also called LESTR, HUMSTSR or fusin), while most macrophage-tropic primary HIV-1 viruses use the CC chemokine receptor CCR5 (see, Feng, Y., et al., *Science* 272:872–877 (1996); Choe, H. et al., *Cell* 85:1135–1148 (1996); Deng. H K., et al., *Nature* 381:661–666 (1996); Dragic, T., et al., *Nature* 381:667–673 (1996); Doranz, B J., et al., *Cell* 85:1149–1158 (1996); and Alkhatib, G., et al., *Science* 272:1955–1958 (1996)), and to an extent CCR3 or CCR2. Primary dual-tropic HIV-1 isolates use CCR5 as well as CXCR4. (See, Zhang, L., et al., *Nature* 383:768 (1996) and Connor, R., et al., *J. Exp. Med.* 185:21–628 (1997)). The macrophage-tropic primary viruses are those most often transmitted from infected to uninfected individuals, and predominate during the long, asymptomatic phase of infection. (See, Cheng-Mayer, C., et al., *Science* 240:80–82; Zhu, T., et al., *Science* 261:1179–1181 (1993); Fenyo, E., *J. Virol.* 62:4414–4419 (1988); Schuitemaker, H., et al., *J. Virol.* 66:1354–1360 (1991); and Connor, R I, et al., *J. Virol.* 67:1772–1778 (1993)). The importance of CCR5 for HIV-1 transmission is underscored by the observation that humans with homozygous defects in CCR5 are relatively resistant to HIV-1 infection. (See, Liu, R., et al., *Cell* 86:367–378 (1996); Samson, M., et al., *Nature* 382:722–725 (1996); and Dean M., et al., *Science* 273:1856–1862 (1996)). CCR5 is used as a corrector by almost all primary HIV-1 isolates regardless of geographic clade, and is used by the related human and primate immunodeficiency viruses, HIV-2 and simian immunodeficiency virus, SIV. (See, Marcon, L., et al., *J. Virol* 71:2522–2527 (1997); Chen, Z., et al., *J. Virol.* 71:2705–2714 (1997); and Cocchi, F., et al., *Science* 270: 1811–1815 (1995)). This suggests that at least part of the viral binding site for CCR5 is well-conserved among these immunodeficiency viruses. While these gp120 structures are under investigation and have yet to be completely defined, mutagenic studies have suggested that elements of the V3 loop may constitute part of the chemokine receptor binding site. Genetic studies of viruses with chimeric HIV-1 envelope glycoproteins containing different V3 loops demonstrated that the gp120 V3 region is a major determinant of which chemokine receptor, CCR5 or CXCR4, can be used as an entry cofactor. (See, Cocchi, F., et al., *Nature med.,* 2:1244–1247 (1996); and Speck, R., et al., *J. Virol.* (in press)). Thus, even in the relatively variable background of the V3 domain, there may exist conserved structural features that collaborate with other conserved gp120 structures to create a high-affinity binding site for CCR5.

It is likely that the interaction of the gp120-CD4 complex with the appropriate chemokine receptor promotes additional conformational changes in the envelope glycoprotein complex. By analogy with the influenza hemoglutinin, it has been suggested that the HIV-1 gp41 ectodomain undergoes major conformational changes during virus entry. (See, Carr, C M., et al., *Cell* 73:823–832 (1993); Chen, C H., et al., *J. Virol.* 69:3771–3777 (1995); Bullough, P., et al. *Nature* 371:37–43 (1994); and Weissenhorn, W., et al., *EMBO J.* 15:1507–1514 (1996)). The proposed result of these changes is the insertion of the hydrophobic gp41 amino terminus (the "fusion peptide") into the membrane of the target cell. Mutagenic analysis and the recently determined crystal structures of HIV-1 gp41 ectodomain fragments are consistent with this model (see, Freed, E., et al., *Proc. Natl. Acad. Sci USA* 87:4650–4654 (1990)).

The exposed nature of the HIV-1 envelope glycoproteins on the surface of virions or infected cells renders them prime targets for the antiviral immune response. In fact, the only viral proteins accessible to neutralizing antibodies are the envelope glycoproteins. Neutralizing antibodies appear to be an important component of a protective immune response, in chimpanzees challenged with HIV-1 (see, Berman, P W., et al., *Nature* 345:622–625 (1990); Girard, et al., *Proc. Natl. Acad. Sci. USA* 88:542–546 (1991); Emini, et al., *Nature* 355:728–730 (1991); and Bruck, et al., *Vaccine* 12:1141–1148 (1994). That neutralizing antibodies generated during the course of HIV-1 infection do not provide permanent antiviral effect may in part be due to the generation of neutralization escape virus variants (see, Nara, et al., *J. Virol.* 64:3779–3791 (1990); Gegerfelt, et al., *Virology* 185:162–168 (1991); and Arendrup, et al., *J AIDS* 5:303–307 (1992)), and to the general decline in the host immune system associated with pathogenesis.

HIV-1 neutralizing antibodies are mostly directed against linear or discontinuous epitopes of the gp120 exterior envelope glycoprotein. Rare examples of gp41-directed neutralizing antibodies have also been documented (see, Muster, et al., *J. Virol.* 67:6642–6647 (1993)). Neutralizing antibodies that arise early in infected humans and that are readily generated in animals by immunization are primarily directed against linear neutralizing determinants in the third variable (V3) loop of gp120 glycoprotein (see, Matthews, et al., *Proc. Natl. Acad. Sci. USA* 83:9709–9713 (1986); and Javaherian, et al., *Science* 250:1590–1593 (1990)). These antibodies generally exhibit the ability to neutralize only a limited number of HIV-1 strains, although some subsets of anti-V3 antibodies recognize less variable elements of the region and therefore exhibit broader neutralizing activity (see, Ohno, et al., *Proc. Natl. Acad. Sci. USA* 88:10726–10729 (1991); Moore, et al., *J. Virol.* 69:122–133 (1995); and Gorny, et al., *J. Virol.* 66:7538–7542 (1992)). Envelope glycoprotein variation within the linear V3 epitope and outside of the epitope can allow escape of viruses from neutralization by these antibodies (see, McKeating, et al., *J. Virol.* 67:4932–4944 (1993)). The second variable (V2) region of the HIV-1 envelope glycoprotein has also been shown to be a target for strain-restricted neutralizing antibodies (see, Fung, et al., *J. Virol.* 66:848–856 (1992); Moore, et al., *J. Virol.* 67:6136–6151 (1993)). Most of the V2 epitopes consist of continuous but conformation-dependent determinants.

Later in the course of HIV-1 infection of humans, antibodies capable of neutralizing a wider range of HIV-1 isolates appear (see, Profy, et al., *J. Immunol.* 144:4641–4647 (1990); Berkower, et al., *J. Em. Med.* 170: 1681–1695 (1989); Ho, et al., *J. Virol.* 489–493 (1991); Kang, et al., *Proc. natl. Acad. Sci. USA* 88:6171–6175 (1991); Steimer, et al., *Science* 254:105–108 ((1991); and Moore et al., *J. Virol.* 67:863–875 (1993)). These broadly-neutralizing antibodies have been difficult to elicit in animals (see, Rusche et al., *Proc. Natl. Acad. Sci. USA* 84:6924–6928 (1987); Klaniecki et al., *AIDS Res. Hum. Retro.* 7:791–798 (1991); and Haigwood, et al., *J. Virol.* 66:172–182 (1992)), and are not merely the result of additive anti-V3 loop reactivities against diverse HIV-1 isolates that accumulate during active infection. A subset of the broadly reactive antibodies, found in most HIV-1-infected individuals, interferes with the binding of gp120 and CD4. At least some of these antibodies recognize discontinuous gp120 epitopes (the so-called CD4BS epitopes) present only on the native glycoprotein. Human monoclonal antibodies derived from HIV-1-infected individuals have been identified that recognize the gp120 glycoproteins from a diverse range of HIV-I isolates, that block gp120-CD4 binding, and that neutralize virus infection (see, Posner, et al., *J. Immunol.* 146:4325–4332 (1991); and Tilley, et al., *Res. Virol.* 142:247–259 (1991)). Some of these CD4BS-directed antibodies efficiently neutralize primary HIV-1 isolates (see, Burton, et al., *Science* 266:1024–1027 (1994)), which are generally more resistant to neutralization than are viruses passaged in immortalized cell lines (see, Daar, et al., *Proc. Natl. Acad. Sci. USA* 87:6574–6578 (1990); Wrin, et al., *J. virol.* 69:39–48 (1995); Sullivan, et al., *J. Virol.* 69:4413–4422 (1995); Sawyer, et al., *J. Virol.* 67:1342–1349 (1994); Moore, et al., *J. Virol.* 69:101–109 (1995); and D'Souza, et al., *J. Infect. Dis.* 175:(in press)(1997)). The discontinuous epitopes recognized by many of the human monoclonal antibodies directed against the CD4BS epitopes have been characterized by mutagenic analysis (see, Thali, et al., *J. Virol.* 65:6188–6193 (1991); Thali, et al., *J. Virol.* 66:5635–5641 (1992); McKeating, et al., *Virology* 190: 134–142 (1992)). Amino acid changes in seven discontinuous gp120 regions, four of which overlap regions defined to be important for CD4 binding, disrupt recognition by these antibodies and, in some cases, allow the generation of neutralization escape mutants.

A second group of neutralizing antibodies found in a smaller number of HIV-1-infected humans is directed against conserved gp120 epitopes that are exposed better upon CD4 binding (see, Thali, et al., *J. Virol.* 67:3978–3988 (1993)). These epitopes, referred to as the CD4-induced (CD4i) epitopes, are extremely sensitive to conformational changes in the gp120 glycoprotein. The integrity of these epitopes is affected by gp120 amino acid changes in the conserved stem of the V1/V2 stem-loop structure and in the C4 region. The CD4i epitopes have been shown to be proximal to the V3 loop and to be masked by the V1/V2 variable loops (see, Wyatt, et al., *J. Virol.* 69:5723–5733 (1995); and Moore, et al., *J. Virol* 70:1863–1872 (1996)). It has been shown that CD4 binding induces a movement of the V 1/V2 loops that exposes the CD4i epitopes. Interestingly, it has been shown that neutralizing antibodies directed against either the V3 loop or the CD4i epitopes block the ability of gp120-CD4 complexes to bind CCR5. Thus, it appears that the major groups of neutralizing antibodies generated in HIV-1-infected humans block the binding of virus to its cellular receptors., either CD4 or the chemokine receptors.

The development of an HIV-1 vaccine as explained above has been hampered by the inefficiency with which antibodies directed against the more conserved gp120 structures are elicited. Most of the antibodies elicited by the HIV-1 envelope glycoproteins, either in infected humans or chimps or in animals immunized with envelope glycoprotein preparations, are not able to neutralize virus. Many of these non-neutralizing antibodies are directed against gp120 structures that are inaccessible on the native envelope glycoprotein complex due to interaction with the gp41 ectodomain (see, Wyatt, et al., (1997)). When neutralizing antibodies are elicited, these are often directed against variable portions of the HIV-1 envelope glycoproteins. Most of the neutralizing antibodies elicited by native HIV-1 gp120 or gp160 glycoproteins are directed against the V3 loop (see, Haigwood, et al., *AIDS Res. Hum. Retro.* 6:855–869 (1990)). Multiple immunizations with native gp120 or gp160 glycoproteins are required to elicit even low titers of neutralizing antibodies with broader strain reactivity. This same pattern of elicitation of neutralizing antibodies has been observed in HIV-1-infected humans or chimps, with antibodies directed against the V3 loop appearing earlier in infection. These results suggest that the structure of the HIV-1 gp120 envelope glycoprotein has evolved to decrease the immunogenicity of particular epitopes in which variation is poorly tolerated by the virus. By the time immune responses to these epitopes are elicited, immune compromise has occurred, viral burden is high, and virus variation and the potential for neutralization escape has reached significant levels. These considerations suggest that use of the native, complete HIV-1 glycoprotein as an immunogen will most efficiently elicit the same types of immune responses that the virus has evolved to evade most efficiently. Improved immunogens based upon the envelope protein are necessary.

Previous studies have indicated that the relatively poor surface accessibility of the more conserved gp120 epitopes related to the CD4 and chemokine receptor binding sites may in part provide an explanation for the low apparent immunogenicity of these regions.

One approach to improve the immunogenicity of gp120 polypeptides has been to remove at least a portion of the "masking" variable loops while retaining the overall conformation of the polypeptide so that it approximates that of the native gp120. This can be done by appropriate selection of amino acid residues to permit the structure to turn. In this manner the conserved conformational epitopes are more exposed and can be used to generate antibodies to these conserved epitopes. Additional improvements in generating such polypeptides would be useful. The V1/V2 and V3 variable loops of the HIV-1 gp120 glycoprotein have been shown to mask the CD4BS epitopes, and removal of these variable regions results in a 5-50-fold increase in exposure of most of the CD4BS epitopes, on both the monomeric and the multimeric envelope glycoproteins. Removal of the V1 and V2 variable loops results in an increased exposure of HIV-1 gp120 epitopes (V3 and CD4i epitopes) located near the binding site for the chemokine receptors. Thus, both of the receptor-binding regions of the HIV-1 gp120 glycoprotein are partially masked by the large variable loop structures of the glycoprotein.

It is imperative that means of efficiently eliciting an array of antibodies directed against the more conserved gp120 elements be developed.

SUMMARY OF THE INVENTION

We have now found polypeptides that are modified from a primate lentivirus envelope glycoprotein such as the HIV-1 envelope glycoproteins that can improve the stability and/or enhance immunogenicity of neutralization epitopes, particularly those conserved on different primary viruses such as the CD4BS and/or CD4i epitopes. The modifications include the deletion of particular variable loops and/or stabilization of functionally relevant envelope glycoprotein structures through the formation of internal disulfide bonds. For example, we have found that introducing cysteine residues at at least one of the following pairs of amino acid residues results in the formation of disulfide bonds and substantially stabilizes the structure of the protein:

Pro 118*--Ala 433

Leu 122--Gly 431

Phe 210--Gly 380

Ser 256--Phe 376

The numbering is based upon HXBc2 numbering and can readily be extrapolated to other viruses and strains.

Preferably disulfide bonds are introduced at either Pro118→Ala433, Leu122-Gly431, Phe210-Gly380, or Ser256-Phe376.

Alternatively, or in addition, one can fill the cavities discovered in the interior of HIV-1 gp120 with hydrophobic residues such as Ser375→Trp, Val155→Trp, Arg273→Trp, Ser481→Phe, Ser447→Ile. These cavity-filling substitutions should stabilize a native HIV-1 gp120 conformation.

Alternatively, or in addition, one can introduce prolines at defined turn structures such as Ile423→Pro, thus stabilizing these turn structures in the gp120 "bridging sheet," which appear to be conformationally flexible (see below).

Alternatively, or in addition, one can increase the hydrophobicity across the interface between the gp120 domains such as Asn377→Leu, Thr283→Ile, and Asp477→Leu. These substitutions are predicted to decrease interdomain flexibility.

These changes can be inserted in a polypeptide that contains all the variable regions, or more preferably, into a polypeptide wherein at least a portion of a variable region, preferably the V1/V2 loops, has been deleted with a linker amino acid residue inserted to retain turns in the structure so that it approximates the conformation of at least one discontinuous conformation epitope of the native envelope protein such as CD4BS or CD4i epitopes.

BRIEF DESCRIPTION OF THE FIGURES

FIG. 1A shows a ribbon drawing of the HIV-1 gp120 glycoprotein complexed with CD4. The perspective is that from the target cell membrane. The two amino-terminal domains of CD4 are shown in blue. The gp120 inner domain is colored red, the outer domain is colored yellow, and the "bridging sheet" is orange. The gp120 residues in which changes resulted in a ≧90% decrease in CCR5 binding are labeled. The V1/V2 stem and the base of the V3 loop (strands β12 and β13 and the associated turn) are indicated.

FIG. 1B shows a molecular surface of the gp120 glycoprotein from the same perspective as that of FIG. 1A. Colored surfaces are associated with gp120 residues in which changes resulted in either a ≧75% decrease (yellow), a ≧90% decrease (red) or a ≧50% increase (green) in CCR5 binding, when CD4 binding was at least 50% of that seen for the wtΔ protein.

FIG. 1C shows the surface depicted in FIG. 1B colored according to the degree of conservation observed among primate immunodeficiency viruses (25). Red indicates conservation among all human and simian immunodeficiency viruses; orange indicates conservation among all HIV-1 isolates, including group O and chimpanzee isolates; yellow indicates modest variability and green indicates substantial variability among HIV-1 20 isolates.

FIG. 1D shows the molecular surface of the gp120 glycoprotein, indicating residues in which changes resulted in a ≧70% decrease in 17b antibody binding, in the absence of sCD4.

FIG. 1E shows the molecular surface of the gp120 glycoprotein, indicating residues in which changes resulted in a ≧70% decrease in CG10 antibody binding in the presence of sCD4. Residues in which changes significantly decreased CD4 binding (and thus indirectly decreased CG10 binding) are not shown. Images were made with Midas-Plus (Computer Graphics Lab, University of California, San Francisco) and GRASP.

FIG. 3A shows the molecular surface of the gp120 core The modeled N-terminal gp120 core residues, V4 loop and carbohydrate structures are included. The variability of the molecular surface is indicated, using the color scheme described in FIG. 2. The modeled carbohydrates are colored light blue (complex sugars) or dark blue (high-mannose sugars). The approximate locations of the V2 and V3 variable loops are indicated. Note the well-conserved surfaces near the "Phe 43" cavity and the chemokine receptor-binding site.

FIG. 3B shows a Ca tracing of the gp120 core. The gp120 residues within 4 Å of the 17b CD4i antibody are shown in green. The residues implicated in the binding of CD4BS antibodies20 are shown in red. Changes in these residues significantly affect the binding of at least 25 percent of the CD4BS antibodies listed in Table 1. The residues implicated in 2G12 bindings are shown in blue. The V4 variable loop, which contributes to the 2G12 epitope, 9 is indicated by dotted lines.

FIG. 3C shows the molecular surface of the gp120 core, oriented and colored as in Figure B.

FIG. 3D shows the approximate locations of the faces of the gp120 core, defined by the interaction of gp120 and antibodies. The molecular surface accessible to neutralizing ligands (CD4 and CD4BS, CD4i and 2G12 antibodies) is shown in white. The neutralizing face of the complete gp120 glycoprotein includes the V2 and V3 loops, which reside adjacent to the surface shown. The approximate location of the gp120 face that is poorly accessible on the assembled envelope glycoprotein trimer and therefore elicits only non-neutralizing antibodiesS6 is shown in purple. The approximate location of an immunologically "silent" face of gp120, which roughly corresponds to the highly glycosylated outer domain surface, is shown in blue.

DETAILED DESCRIPTION OF THE INVENTION

Figure 1A:
FIGS. 1A–1E show the structure of the HIV-1 gp120 region implicated in CCR5 binding.

We have discovered a series of novel polypeptides that can (1) enhance the immunogenicity of primate lentivirus envelope proteins for certain conserved epitopes, (2) generate a greater range of antibodies against "masked" gp120 structures and/or (3) stabilize the three-dimensional structure of the molecule.

We have discovered regions where disulfide bonds can be inserted which will stabilize the conformation of the molecule in a conformation approximating the native envelope glycoprotein conformation. We have discovered conserved regions and epitopes that are critical for CD4 and chemokine receptor binding. We have discovered critical turn structures of the molecules as well as internal cavities that decrease the immunogenicity of epitopes that would raise antibodies that could block CD4 binding and/or chemokine binding.

Preferably, the envelope protein is selected from the group consisting of HIV or SIV. More preferably, it is HIV. Still more preferably, it is HIV-1 gp120.

We have succeeded in growing crystals of gp120 (from the HXBc2 HIV-1 strain) in a ternary complex with two-domain CD4 (D 1 D2 sCD4) and the Fab fragment of a CD4i neutralizing antibody, 17b Fab. The crystals diffracted to a minimum Bragg spacing of at least 2.2A, and data have been collected from cryogenically preserved crystals on the native complex as well as on isomorphous heavy atom derivatives.

While some elements of the HIV-1 gp120 structure (e.g. the V3 loop) are not supplied by analysis of these crystals, the vast majority of the gp120 residues are able to be defined in the structure. Importantly, all of the gp120 residues thought to contribute to the CD4BS and CD4i neutralization epitopes are defined in the available structure.

Many of the antibody responses elicited against the HIV-1 envelope glycoproteins during natural infection of humans are incapable of neutralizing the virus. Studies of monoclonal antibodies derived from HIV-1-infected individuals indicate that most of these non-neutralizing antibodies are directed against elements of the gp120 and gp41 glycoproteins that interact on the assembled oligomer. These elements are not accessible on the functional envelope glycoprotein spike on the virus membrane or infected cell surface, thereby rendering the antibodies directed against them ineffectual at neutralization. The labile association of gp120 and gp41, which exposes and/or creates the epitopes for these non-neutralizing antibodies, apparently represents an adaptive mechanism for lentiviruses such as HIV-1 to divert the humoral immune response under conditions where antigen is limiting.

A corollary is that the gp120 glycoprotein dissociated from the functional oligomer may have evolved to be less effective at eliciting neutralizing antibodies directed against conserved gp120 structures. This corollary appears to be supported by the many attempts to elicit neutralizing antibodies by gp120 immunogens over the past several years. Dissociation from gp41 apparently results in an increase in the conformational flexibility of the gp41-interactive regions of gp120, predisposing the gp120 glycoprotein to elicit non-neutralizing antibodies preferentially over the more broadly neutralizing antibodies. This conformational flexibility can have two consequences relevant to selective elicitation of non-neutralizing antibodies:

1) The flexibility and surface exposure of the gp41-interactive C1 and C5 regions on free gp120 can make these structures more immunogenic; and 2) Conformational flexibility in the C1 and C5 regions, can mask many CD4BS epitopes, may disrupt these epitopes and decrease the efficiency with which CD4BS-directed antibodies are elicited.

Thus, we have found a number of positions where disulfide bonds can be introduced to stabilize the polypeptide's structure. This is important given the structure of the molecule.

Figure 1B:
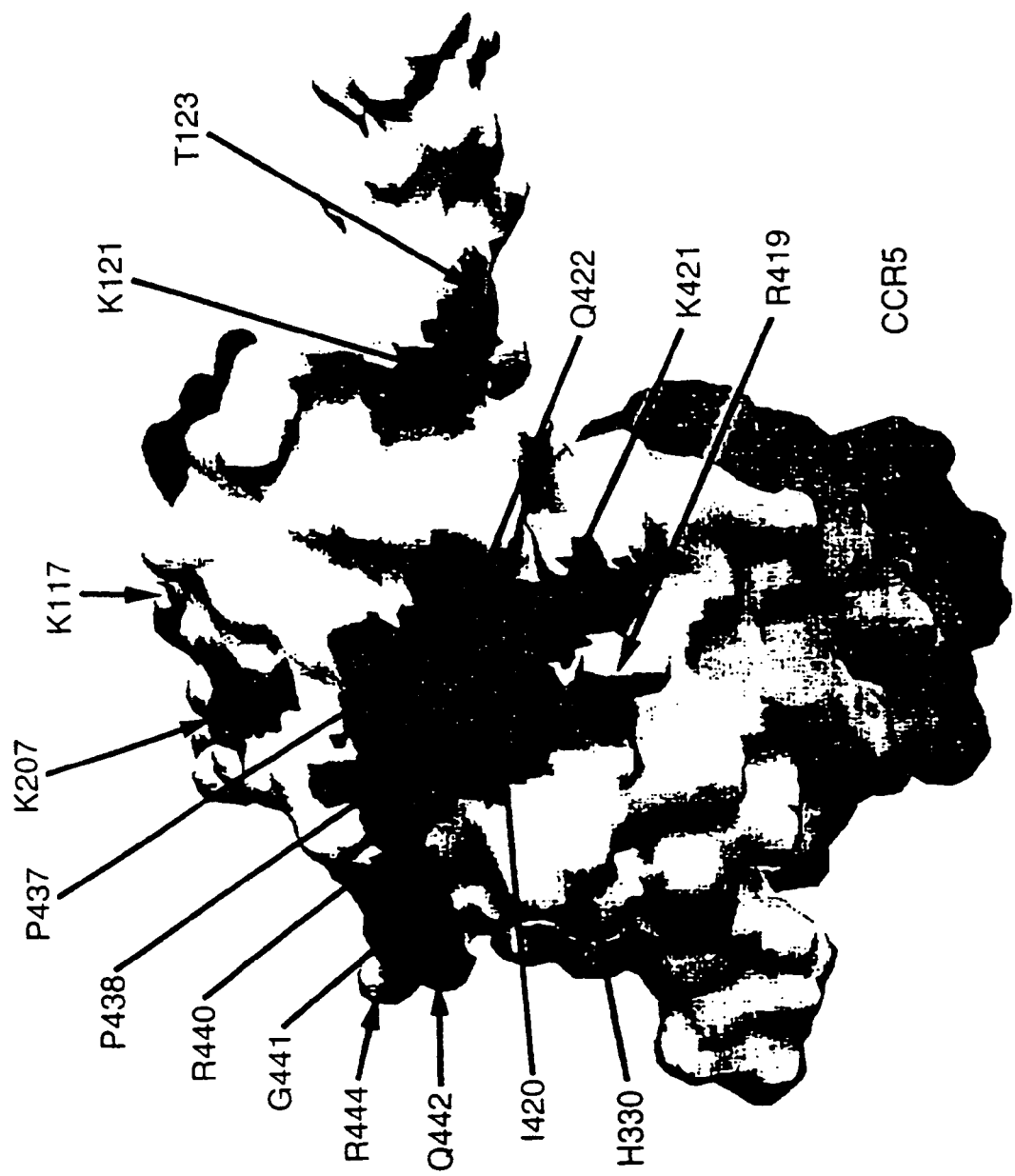
Figure 1C:
Figure 1D:
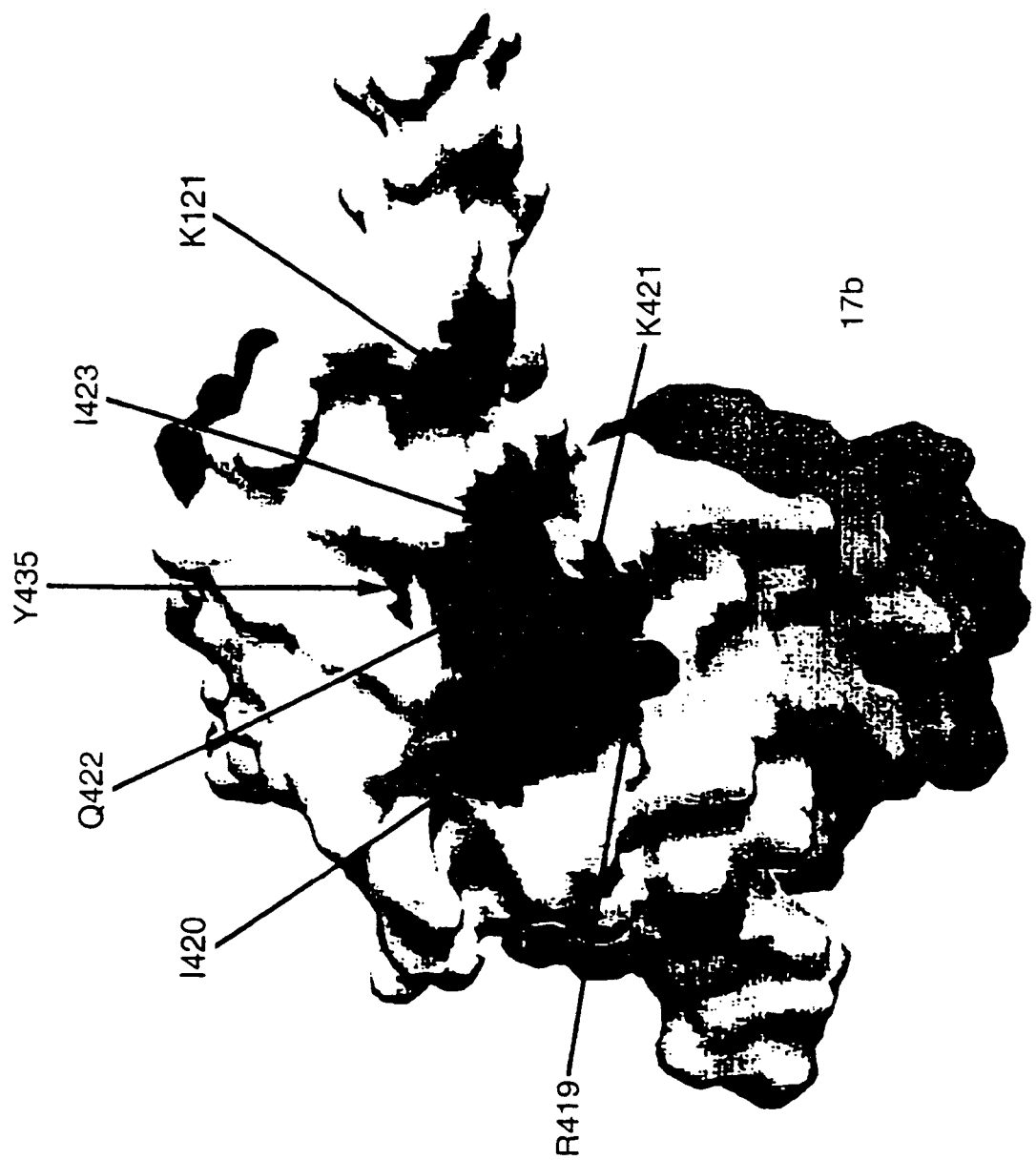
Figure 1E:
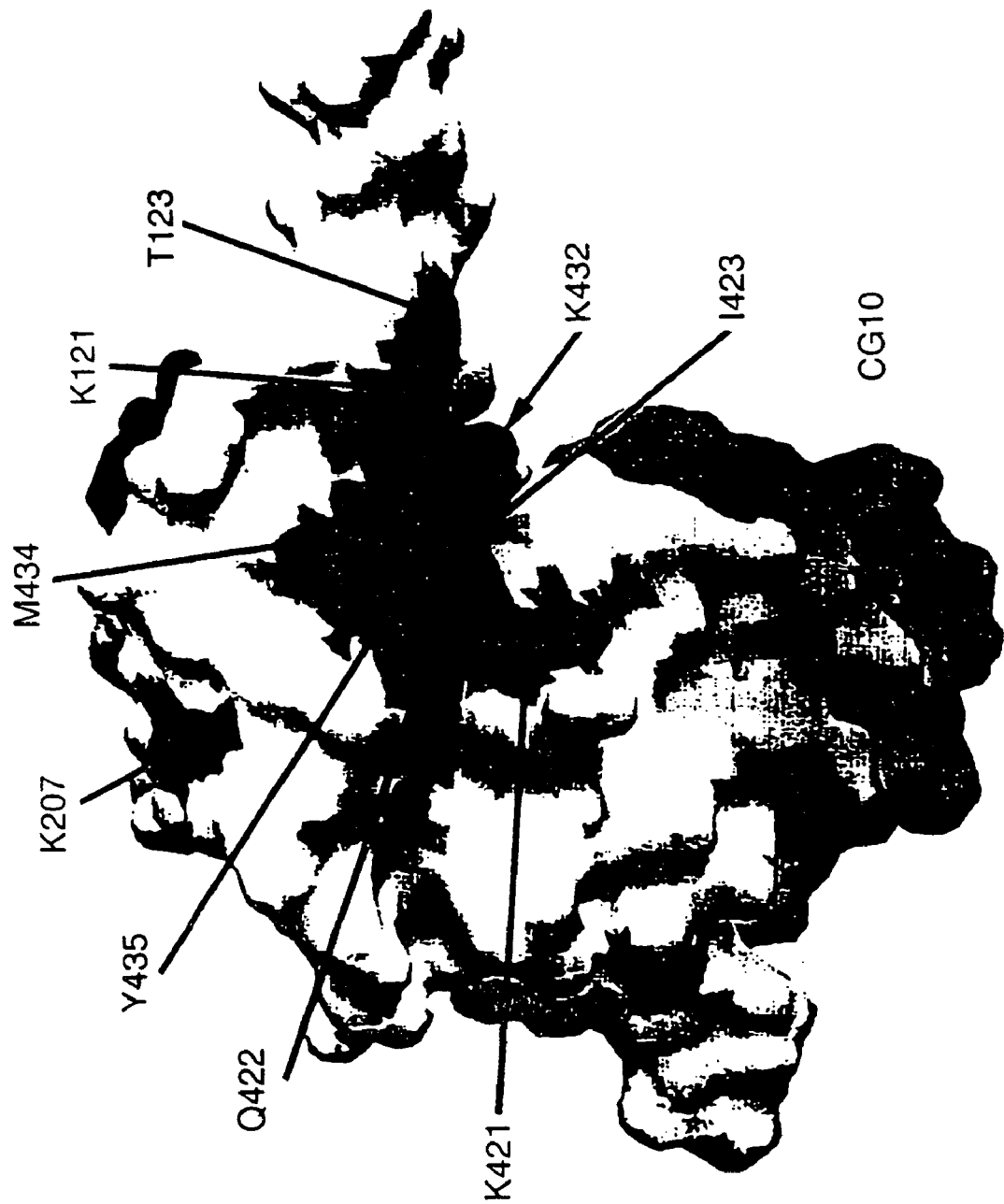

For example, the gp120 core is composed of an inner domain, an outer domain, and a "bridging sheet" (FIG. 1A). The "bridging sheet" is a four-stranded, antiparallel β-sheet that includes the V1/V2 stem and strands (β20 and β21) derived from the fourth conserved gp120 region. CD4 contacts gp120 residues in the outer domain and the "bridging sheet". The gp120 residues implicated by our study in CCR5 binding are located near or within the "bridging sheet" (FIGS. 1A and 1B). The "bridging sheet" is predicted to face the target cell after the envelope glycoproteins bind CD4. Even more than the CD4-binding site, the gp120 region implicated in CCR5 binding is highly conserved among primate immunodeficiency viruses; this is particularly apparent in comparison to the remainder of the gp120 surface thought to be exposed on the assembled envelope glycoprotein complex (See FIGS. 1C and 2). The CD4i epitope for the 17b antibody is located near or within the "bridging sheet", consistent with the ability of the antibody to block CCR5 binding. All of the individual gp120 residues in which changes disrupted recognition by the 17b antibody (FIG. 1D) are located close to the gp120-17b interface in the crystallized complex (Table 1). The binding of another antibody, CG10, which disrupts gp120-CCR5 interaction and competes with the 17b antibody for gp120 binding, is also affected by changes in amino acid residues within or near the "bridging sheet" (FIG. 1E). The position and orientation of the V3 base in the structure, in conjunction with a number of mutagenic and antibody competition studies, indicates that the gp120 V3 loop resides proximal to the region implicated in CCR5 binding (FIG. 1A). For example, the binding of both CG10 and CD4i antibodies to gp120 can be disrupted by some V3 changes. Furthermore, several V3-directed antibodies compete with CD4i antibodies for gp120 binding.

We have discovered that the CCR5-binding site is likely composed of conserved gp120 elements near or within the "bridging sheet" and V3 loop residues. The latter apparently includes more conserved structures (e.g. the aromatic or hydrophobic residue at position 317), as well as more variable structures that determine the specific chemokine receptor used. Some of the gp120 residues identified in this and previous studies as determinants of chemokine receptor utilization can modulate the interaction of the V3 loop and elements near the "bridging sheet". Studies of HIV-1 revertants suggested a functional interaction of gp120 residue 440, shown here to influence CCR5 binding, with the V3 loop.

A subset of the gp120 residues in or near the "bridging sheet" apparently contacts CCR5 directly. Most of the gp120 residues implicated in CCR5 binding exhibit reasonable solvent accessibility in the free gp120 core (Table 1). The gp120 surface implicated in CCR5 binding is highly basic, favoring interactions with the acidic CCR5 amino terminus, which has been shown to be important for gp120 binding. Additional, hydrophobic interactions, similar to those seen for gp120-17b binding, can also contribute to the gp120-CCR5 interaction.

The exposure and/or formation of the CCR5-binding site of HIV-1 gp120 glycoproteins is dependent upon interaction with CD4. CD4 binding has been shown to reposition the V1/V2 variable loops and thus expose the CD4i epitopes, which overlap the CCR5-binding region. However, since a gp120 glycoprotein lacking the V1 and V2 variable loops also exhibits CD4-dependent CCR5 binding, the interaction with CD4 must cause other conformational changes in gp120 related to the CCR5-binding site. Our results, which highlight the proximity of the two receptor-binding sites on gp120, help explain the induction of such conformational changes. First, one of the components of the "bridging sheet", the V1/V2 stem, also contacts CD4. Thus, CD4 binding, which appears to distort the V1/V2 stem, may reposition this structure and allow the formation of the β-sheet important for CCR5 binding. In this respect, a substitution of aspartic acid for threonine 123, which is located in the V1/V2 stem and contacts CD4, significantly decreases CCR5 binding. This substitution can disrupt CD4-induced conformational changes in the V1/V2 stem required for CCR5 binding. Second, the CD4-bound conformation of gp120 exhibits a cavity (the "Phe 43" cavity) within the gp120 interior. This cavity contacts the gp120 inner and outer domains as well as the "bridging sheet" and likely forms as a result of interdomain conformational changes in gp120 induced by CD4 binding. Since the "bridging sheet" lacks its own hydrophobic core and is thus dependent upon residues contributed by both inner and outer domains, any shift in orientation between these domains would alter the conformation of the "bridging sheet". Furthermore, CD4 binding could also alter the precise orientation of the "bridging sheet" with respect to the inner and outer domains, thus aligning the V3 loop and conserved gp120 elements important for CCR5 binding.

CD4 binding induces conformational changes within the "bridging sheet" as well as between this sheet and the inner and outer domains to form the high-affinity CCR5 binding site. For some primate immunodeficiency viruses, the CD4-bound conformation of gp120 must be energetically assessable in the absence of CD4, which would explain the documented examples of CD4-independent chemokine receptor binding and entry.

The CCR5-binding region defined in this study using HIV-1 is also important for the binding of the other primate lentiviruses such as simian, and of human immunodeficiency viruses to other chemokine receptors. The identified region exhibits one of the most highly conserved surfaces on the HIV-1 gp120 glycoprotein, supporting its functional importance for all primate immunodeficiency viruses. The laboratory-adapted HXBc2 envelope glycoprotein, which uses CXCR4 and not CCR5 as a corrector, can be converted to an efficient CCR5-using protein simply by substituting the V3 loop of the YU2 virus. Thus, all of the necessary CCR5-binding region outside of the V3 loop are conserved, as demonstrated by the substitution between the divergent HXBc2 and YU2 viruses. Indeed, we have shown that alteration of the lysine 117, lysine 207 and glycine 441 in the HXBc2-YU2V3 chimeric protein also disrupts CCR5 binding. Consistent with the use of this region for the binding of other chemokine receptors is the observation that the gp120 changes associated with the conversion of HIV-2 to a CD4-independent, CXCR4-using virus affect the "bridging sheet" and the V3 loop. Alterations in "bridging sheet" residues have also been implicated in changes in the tropism of HIV-1 for immortalized cell lines that do not express CCR5. And, the 17b antibody neutralizes HIV-1 strains that use different chemokine receptors, thereby supporting our finding of the involvement of a common gp120 region in chemokine receptor interaction.

Chemokine receptor binding can trigger additional conformational changes in the envelope glycoprotein complex that ultimately lead to the fusion of the viral and target cell membrane. Some of these changes include exposure of the ectodomain of the gp41 transmembrane envelope glycoprotein. The CCR5-binding region defined herein resides close to the trimer axis of the assembled envelope glycoprotein complex. Indeed, some of the gp120 residue changes that affect CCR5 binding also affect the non-covalent association of gp120 and gp41 subunits in the trimeric complex. This indicates that chemokine receptor binding alters the relationship between gp120 and gp41, leading to the exposure of the gp41 ectodomain and interaction with the target cell membrane.

Stabilizing the structure of an envelope protein such as the gp120 glycoprotein should improve the ability of the glycoprotein to elicit desirable neutralizing antibody responses. This follows from our observation that all of the conserved HIV-1 gp120 neutralization epitopes span gp120 domains that exhibit potential flexibility. Stabilization of the gp120 structure can be achieved by introducing new disulfide bridges at specific locations on the gp120 chain. This targeted introduction of disulfides is designed to maintain the molecule in a conformation wherein at least the CD4BS or CD4i epitopes approximate the wild-type conformation. We expect this disulfide bonding to preserve the integrity of the relevant neutralization epitopes.

The disulfide bonds can be introduced at a number of different amino acid residues in the gp120 structure. The only precaution is not to replace an amino acid residue critical for the generation of an antibody to a conserved epitope. A number of these epitopes are set forth in the tables generated by the binding assay. Residues that can be used include Pro118-Ala433 (using HXBc2 numbering), Leu122-Gly431, Phe210-Gly380, and Ser256-Phe376. The respective amino acid residues in other strains can readily be derived by standard means such as aligning the amino acid sequence by any standard computer homology program (e.g. these include, but are not limited to BLAST 2.0 such as BLAST 2.0.4 and 2.0.5 available from the NIH (See www.ncbi.nlm.nkh.gov/BLAST/newblast.html) (Altschul, S. F., et al. Nucleic Acids Res. 25: 3389–3402 (1997))and DNASIS (Hitachi Software Engineering America, Ltd.) under the default setting. Preferably one inserts disulfide bonding at one of Pro-Ala or Leu-Gly and one of Phe-Gly or Ser-Phe.

In addition, other residues that can be used can be determined based upon the following criteria:

1) The two residues targeted for cysteine substitution are distant on the gp120 linear sequence, thus increasing the entropic benefit of the cysteine bridge (see below);

2) The C atoms of the selected residues are within 6× of one another and the $C_\beta$, atoms within 4× of each other, in the native gp120 structure;

3) Neither of the selected residues is proximal in the structural model to naturally occurring gp120 cysteines, nor do natural disulfide bonds already link the targeted gp120 strands;

4) The substituted residues as aforesaid, do not make major contributions to the binding of desired neutralizing antibodies;

5) If internal residues are chosen, both residues are involved in mutual packing interactions.

Adherence to these criteria should optimize the opportunity to generate well-folded gp120 glycoprotein derivatives in which the natural disulfide bonds form and the introduced cysteines create an additional novel disulfide bond. Within a 6× inter-C distance, the possibility for either cis- or trans-disulfide bond formation allows considerable flexibility in interatomic distances.

These choices can be further confirmed by taking the overall energy considerations into account. For example, theoretical and empirical studies of the effects of added covalent cross-links on the folded state have been conducted on model proteins (see, Hazes, et al., *Protein Eng.* 2:119–125 (1988); Muskai et al., *Protein Eng.* 3:667–672 (1990); Reiter, et al., *Protein Eng.* 8:1323–1331 (1995); Sowdhamini, et al., *Protein Eng.* 3:95–103 (1989); Zhou, et al., *Biochem* 32:3178–3187 (1993); Johnson, et al., *Biochem.* 17:1479–1483 (1978); and Pace, et al., *J. Biol. Chem.* 263:11820–11825 (1988)). Most proteins can be modeled as existing in two states, native and unfolded, the ratio of which at any given temperature, pH and salt concentration can be specified by an equilibrium constant $K_F$ (see. Kyte, et al., *Structurei n Protein Chemistry pp.* 445–466 (1995)). The equilibrium constant of folding ($K_F$) is related to the standard free energy of folding ( )G°$_F$) by the equation)G°$_F$=RT in $K_F$, where R is the gas constant and T is the temperature. The)G° F. value is primarily the sum of the favorable enthalpic contribution of removal of hydrophobic amino acids from contact with the aqueous environment and the unfavorable loss of configurational entropy of the unfolded, random coil. Under physiologic conditions, the)G° F. value for most proteins is slightly negative (−30 to −60 kJ/mole), thus favoring the native conformation.

The introduction of disulfide or other covalent bonds cross-linking strands of a protein has been demonstrated to stabilize the native state of the protein, lowering the)G° F. value. Since proteins must be already folded to allow cysteines that are adjacent in the native structure to form a disulfide bond, and cysteine bridges per se contribute little to enthalpic changes favorable to folding, the vast majority of the stabilizing effect of disulfide bonds on the native state derives from a decrease in the configurational entropy of the unfolded protein. A practical consequence of this is that the greater the distance in the linear amino acid sequence between the two cysteines that are cross-linked, the greater the magnitude of the stabilizing effect on the native conformation. These theoretical considerations have been supported by experiments introducing cross-links into proteins at various positions and determining the resulting $K_F$ and) $G°_F$ values. The decreases in)G° F. associated with cross-linking in these experiments were on the order of −20 kJ/mole, which can exert considerable effects on stabilization of native structure (considering that the difference between unfolded and native status is typically only −30 to −60 kJ/mole). Since the existing intrachain disulfide bridges in the HIV-1 gp120 glycoprotein only minimally constrain the potential conformations available to the denatured protein, a significant benefit should accrue by introducing additional, properly positioned cross-links.

The gp120 exists in three domains, and the presence of cavities wedged between these domains offers the possibility of interdomain flexibility. Since the conserved neutralization epitopes on gp120 span two domains, such flexibility can render the protein incapable of efficiently eliciting these kinds of desirable antibodies. The selective use of introducing hydrophobic amino acid residues in the modified envelope protein can enhance immunogenicity as discussed below.

The disulfide stabilized mutants can be created by the site-directed mutagenesis of a plasmid designed to express the soluble HIV-1 gp120 glycoprotein in the supernatants of *Drosophila* cells by known means. For example, 89.6 and YU2 gp120 or any other gp120 glycoproteins can be used. Cell supernatants can be examined for the production of properly folded gp120 glycoproteins, using a pool of sera from HIV-1-infected humans, which will recognize even misfolded gp120 molecules, and a panel of conformation-dependent anti-gp120 monoclonal antibodies. Properly folded proteins with desirable epitopes intact will be purified by immunoamnity chromatography using a CD4BS-directed antibody (F105) column.

Several methods are available to document the formation of, for example, the desired disulfide bond in the gp120 glycoprotein. Chemical methods allow an estimate of the percentage of the proteins in a given preparation that form the disulfide bond. For example, ethylenimine reacts with cysteine under mild conditions to form an S-($_\beta$aminoethyl)-cysteine derivative, which can be detected in protein hydrolysates by chromatographic analysis. The presence of these derivatives indicates that at least some of the cysteines in the protein are free, and the percentage of these unpaired cysteines can be estimated by using other methods that do not distinguish cysteine from cystine (e.g., ethylenimine in conjunction with a reducing agent, or performic acid oxidation (Rafferty, *Biochem. Biophys. Res. Commun.* 10:467 (1963); and Moore, S., *J. Biol. Chem.* 238:235 (1963)). Analysis of proteolytic fragments of the wild-type and mutant glycoproteins is a second approach capable of documenting the formation of the desired disulfide bond. The latter method can be used in conjunction with monoclonal antibodies directed against specific linear peptides of gp120 to verify that peptides in the vicinity of the putative disulfide bond exhibit altered behavior upon proteolysis of wild-type and mutant glycoproteins.

The formation of an additional disulfide bond bridging linearly distant gp120 regions that are not already constrained by existing disulfide bonds should result in a significant effect on $K_F$ and)G° F. Since under physiological conditions, most proteins are stably folded in their native state, estimates of $K_F$ and)$G°_F$ are typically made under conditions of low pH, higher temperature and/or the presence of urea or guanidinium chloride. Since the protein folding reaction must occur reversibly to obtain estimates of $K_F$ or)$G°_F$, the test should avoid the use of high temperatures that often lead to irreversible changes in proteins. Instead, the denaturation of the wild-type and cross-linked mutant gp120 glycoproteins should be compared over a range of chaotropic salt concentrations and pH values. A number of physical properties of proteins have been used to monitor protein folding, including intrinsic viscosity, optical rotation, molar ellipticity, ultraviolet light absorption, electrophoretic mobility and sedimentation velocity. Absorption of ultraviolet light can be studied for the wild-type and mutant gp120 glycoproteins produced in *Drosophila* cells, since this parameter is easily measured and reliably detects changes in protein folding. The two states of gp120, native and denatured, exist, $K_F$ and)G° F. can be determined for each concentration of guanidinium chloride, temperature and pH directly from the absorbance versus salt/pH curves. Typically, $K_F$ and)G° F. values obtained under these varying conditions are used to extrapolate to physiologic salt and pH values, although the stabilizing effect of the introduced disulfide should be evident over a wide range of pH and chaotropic salt concentrations.

As mentioned above, one can also alternatively introduce Pro at defined turn structures. For example, at Ile423. These changes can readily be made and tested, specifically to see that the integrity of relevant neutralization epitopes is retained.

To enhance the ability to generate antibodies one can increase the hydrophobicity of various cavities in the molecule. The presence of cavities in the CD4-bound gp120 structure probably reflects interdomain flexibility in the non-CD4-bound portion. The interdomain flexibility could decrease the integrity of CD4BS and CD4i epitopes, and other conserved structures.

One way of dealing with this problem is to increase the hydrophobic residues in the cavity. Hydrophobic residues are well-known and include Trp, Phe, Leu, and Ile. One can change some of the non-hydrophobic residues into hydrophobic residues, or increase the hydrophobicity of already hydrophobic residues. An increase in the size of the side chain can be tolerated, depending on the volume of the cavity to be filled. The changes can be made by site-directed mutagenesis or other known means. The changes can be tested for their effect on antibody binding by using a panel of known antibodies that bind to a desired epitope, e.g., using CD4BS epitopes. Examples of the changes that can be made include Ser375→Trp, Val255→Trp, Arg273→Trp, Ser481→Phe, and Ser447→Ile. Preferably, at least one of the amino acid residues in the cavity are changed, i.e., they are Trp or Phe or Ile, instead of the wild-type configuration.

The recessed nature of the CD4 binding pocket may delay the generation of high affinity antibodies against the CD4BS epitopes and can afford opportunities to minimize the antiviral efficacy of such antibodies once they are elicited. The degree of recession is believed to be even greater on the full length glycosylated gp120 than is evident on the crystallized gp120 core. The recessed pocket is flanked on one side by the V1/V2 stem loop structure. The V2 loop apparently folds back along the V1/V2 stem with V2 residues 183–188 proximal to Asp 368 and Glu 370. This can enhance masking of the adjacent CD4BS and CD4i gp120 epitopes and divert antibody responses toward the variable loops. This may be dealt with by using gp120 polypeptides where at least a portion of the variable loop has been deleted as described in U.S. Pat. No. 5,817,316.

Still more preferably, more than one of the amino acid residues have these changes.

One can also increase the hydrophobicity across the interface between the gp120 domains. Hydrophobic residues that fill the interdomain cavities will decrease interdomain flexibility.

Thus, one should increase the generation of antibodies by the conserved receptor-regions, and can enhance immunogenicity or raise a greater number of antibodies to these desired sites than the wild-type protein does. This can be done by having the polypeptide contain hydrophobic residue at certain interface sites instead of other residues. For example, having Leu, Ile, Trp, etc., such as Leu instead of Asn377, Ile instead of Thr283, and/or Leu instead of Asp477. The key to the substitution is to preserve the conformational integrity of the desired neutralization epitope, while at the same time filling the interdomain cavities.

The integrity of relevant neutralization epitopes on an envelope glycoprotein such as gp120 can be verified with a panel of monoclonal antibodies, as described above. Purified mutant proteins that exhibit formation of e.g., the desired disulfide bond and increased stability of a native conformation can be used to immunize mice, in parallel with the wild-type gp120 as a control.

The polypeptides of this invention can be used to generate a range of antibodies to gp120. For example, antibodies that affect the interaction with the binding site can be directly screened for example using a direct binding assay. For example, one can label, e.g. radioactive or fluorescent, a gp120 protein or derivative and add soluble CD4. There are various soluble CD4s known in the art including a two-domain (D1D2 sCD4) and a four-domain version. The labeled gp120, or derivative, e.g., a conformationally intact deletion mutant such as one lacking portions of the variable loops (e.g. V1/V2) and in some instances constant regions and soluble CD4 can be added to medium containing a cell line expressing a chemokine receptor that the antibody will block binding to. In this example, the derivative will block binding to CCR5. Alternatively, when using a derivative from a T cell tropic gp120 one would use a cell line that expresses CXCR4. Binding can then be directly measured. The antibody of interest can be added before or after the addition of the labeled gp120 or derivative and the effect of the antibody on binding can be determined by comparing the degree of binding in that situation against a base line standard with that gp120 or derivative, not in the presence of the antibody.

A preferred assay uses the labeled gp120, or derivative portion, for example a gp120 protein derived from an M-tropic strain such as JR-FL, iodinated using for instance solid phase lactoperoxidase (in one example having a specific activity of 20 µCi/µg). The cell line containing the chemokine receptor in this example would be a CCR5 cell line, e.g. L1.2 or membranes thereof. Soluble CD4 would be present.

In one embodiment, the conformational envelope polypeptide, such as gp120 should contain a sufficient number of amino acid residues to define the binding site of the gp120 to the chemokine receptor (e.g. typically from the V3 loop) and a sufficient number of amino acids to maintain the conformation of the peptide in a conformation that approximates that of wild-type gp120 bound to soluble CD4 with respect to the chemokine receptor binding site. Preferably, the V1/V2 loops are deleted. In other embodiments at least portions of the V3 loop can be removed to remove masking amino acid residues. In order to maintain the conformation of the polypeptide one can insert linker residues that permit potential turns in the polypeptides structure. For example, amino acid residues such as Gly, Pro and Ala. Gly is preferred. Preferably, the linker residue is as small as necessary to maintain the overall configuration. It should typically be smaller than the number of amino acids in the variable region being deleted. Preferably, the linker is 8 amino acid residues or less, more preferably 7 amino acid residues or less. Even more preferably, the linker sequence is 4 amino acid residues or less. In one preferred embodiment the linker sequence is one residue. Preferably, the linker residue is Gly.

In one preferred embodiment, the gp120 also contains a CD4 binding site (e.g. from the C3 region residues 368 and 370, and from the C4 region residues 427 and 457). The chemokine binding site is a discontinuous binding site that includes portions of the C2, C3, C4 and V3 regions. By deletion of non-essential portions of the gp120 polypeptide—such as deletions of portions of non-essential variable regions (e.g. V1/V2) or portions in the constant regions (e.g. C1, C5) one can increase exposure of the CD4 binding site. Another embodiment is directed to a gp120 portion containing a chemokine binding site. Similarly, by deleting the non-essential portions of the protein one can increase exposure of the chemokine binding site. The increased exposure enhances the ability to generate an antibody to the CD4 receptor or chemokine receptor, thereby inhibiting viral entry. Removal of these regions is done while requiring the derivative to retain an overall conformation approximating that of the wild-type protein with respect to the native gp120 binding region, e.g. the chemokine binding region when complexed to CD4. In addition, one can remove glycosylation sites that are disposable for proper folding (see Wyatt et al., U.S. provisional application no. EL014417278US, filed Jun. 17, 1998). Maintaining conformation can be accomplished by using the above-described linker residues that permit potential turns in the structure of the gp120 derivative to maintain the overall three-dimensional structure. Preferred amino acid residues that can be used as linker include Gly and Pro. Other amino acids can also be used as part of the linker, e.g. Ala. Examples on how to prepare such peptides are described more fully in Wyatt, R., et al. *J. of Virol.* 69:5723–5733 (1995); Thali, M., et al., *J. of Virol.* 67:3978–3988 (1993); and U.S. Pat. No. 5,817,316, issued Oct. 6, 1998 which are incorporated herein by reference. See for example Wyatt which teaches how to prepare V1/V2 deletions that retain the stem portion of the loop.

In one embodiment the gp120 derivative is designed to be permanently attached at the CD4 binding site to sufficient domains of CD4 to create a conformation of the chemokine binding site approximating that of the native gp120 CD4 complex.

An alternative gp120 derivative is one wherein the linkers used result in a conformation for the derivative so that the discontinuous binding site or a discontinuous epitope such as CD4BS or CD4i with the chemokine receptor approximates the conformation of the discontinuous binding site for the chemokine receptor in the wild-type gp120/CD4 complex. These derivatives can readily be made by the person of ordinary skill in the art based upon the above described methodologies and screened in the assays shown herein to ensure that proper binding is obtained.

The gp120 polypeptide can also be bound to at least a portion of a gp41 polypeptide, namely the coiled coil. Some of these derivatives will lack the gp41 transmembrane region and will therefore be made as secreted, soluble oligomers. For example, gp41 portions lacking the transmembrane region but retaining the cytoplasmic region, others truncated beginning with the transmembrane region. The gp41 polypeptide may contain additional cysteine residues, which result in the formation of the SH bonds between the monomers thereby stabilizing the complex as a trimer having spikes similar to that found in the wild type (as in U.S. application Ser. No. 09/164,880).

These immunogenic oligomers can be used to generate an immune reaction in a host by standard means. For example one can administer the polypeptide in adjuvant. In another approach, a DNA sequence encoding the envelope protein, e.g., the one based upon gp120 can be administered by standard techniques. The approach of administering the protein is presently preferred.

The protein is preferably administered with an adjuvant. Adjuvants are well known in the art and include aluminum hydroxide, Ribi adjuvant, etc. The administered protein is typically an isolated and purified protein. The protein is preferably purified to at least 95% purity, more preferably at least 98% pure, and still more preferably at least 99% pure. Methods of purification while retaining the conformation of the protein are known in the art. The purified protein is preferably present in a pharmaceutical composition with a pharmaceutically acceptable carrier or diluent present.

DNA sequences encoding these proteins can readily be made. For example, one can use the native gp 160 (or a derivatized gp120 portion) of any of a range of primate lentiviruses such as HIV-1 strains which are well known in the art and can be modified by known techniques such as deleting the undesired regions such as variable loops and to insert desired coding sequences such as cysteines and linker segments. In addition to DNA sequences based upon existing strains, the codons for the various amino acid residues are known and one can readily prepare alternative coding sequences by standard techniques.

DNA sequences can be used in a range of animals to express the monomer, which then forms into the trimer and generates an immune reaction.

DNA sequences can be administered to a host animal by numerous methods including vectors such as viral vectors, naked DNA, adjuvant assisted DNA catheters, gene gun, liposomes, etc. In one preferred embodiment the DNA sequence is administered to a human host as either a prophylactic or therapeutic treatment to stimulate an immune response, most preferably as a prophylactic. One can administer cocktails containing multiple DNA sequences encoding a range of HIV env strains.

Vectors include chemical conjugates such as described in WO 93/04701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include herpes virus vectors such as a herpes simplex I virus (HSV) vector [Geller, A. I. et al. *J. Neurochem* 64: 487 (1995); Lim, F. et al., in DNA Cloning: *Mammalian Systems*, D. Glover, Ed. (Oxford Univ. Press, Oxford England) (1995); Geller, A. I. et al., *Proc Natl. Acad. Sci. U.S.A.* 90: 7603 (1993); Geller, A. I., et al., *Proc Natl. Acad. Sci USA* 87: 1149 (1990)], adenovirus vectors [LeGal LaSalle et al., *Science* 259: 988 (1993); Davidson, et al., *Nat. Genet* 3: 219 (1993); Yang, et al., *J. Virol.* 69: 2004 (1995)] and adeno-associated virus vectors [Kaplitt, M. G., et al., *Nat. Genet.* 8:148 (1994)].

The DNA sequence can be operably linked to a promoter that would permit expression in the host cell. Such promoters are well known in the art and can readily be selected. For example, when expression in a mammalian host is desired, a promoter that results in high levels of expression in such host cells is used. Appropriate polyalkenylation sequences are also known and can be selected. Representative examples of such promoters, include a retioviral LTR or SV40 promoter, the *E. coli*. lac or trp, the phage lambda P[L]promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda P[R], P[L]and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by a variety of methods including calcium phosphate transfection, DEAE-Dextran mediated transfection, or electroporation (Davis, L., Dibner, M., Battey. I., *Basic Methods in Molecular Biology*, (1986)).

Stabilized forms of these complexes can readily be made, for example, by conjugates such as a poly(alkylene oxide) conjugate. The conjugate is preferably formed by covalently bonding the hydroxyl terminals of the poly(alkylene oxide) and a free amino group in the gp120 portion that will not affect the conformation of the discontinuous binding site. Other art recognized methods of conjugating these materials include amide or ester linkages. Covalent linkage as well as non-covalent conjugation such as lipophilic or hydrophilic interactions can be used.

The conjugate can be comprised of non-antigenic polymeric substances such as dextran, polyvinyl pyrrolidones, polysaccharides, starches, polyvinyl alcohols, polyacrylamides or other similar substantially non-immunogenic polymers. Polyethylene glycol(PEG) is preferred. Other poly(alkylenes oxides) include monomethoxy-polyethylene glycol polypropylene glycol, block copolymers of polyethylene glycol, and polypropylene glycol and the like. The polymers can also be distally capped with C1–4 alkyls instead of monomethoxy groups. The poly(alkylene oxides) used must be soluble in liquid at room temperature. Thus, they preferably have a molecular weight from about 200 to about 20,000 daltons, more preferably about 2,000 to about 10,000 and still more preferably about 5,000.

One can administer these stabilized compounds to individuals by a variety of means. For example, these antibodies can be included in vaginal foams or gels that are used as preventives to avoid infection and applied before people have sexual contact.

The peptides or antibodies when used for administration are prepared under aseptic conditions with a pharmaceutically acceptable carrier or diluent.

Doses of the pharmaceutical compositions will vary depending upon the subject and upon the particular route of administration used. Dosages can range from 0.1 to 100,000 μg/kg a day, more preferably 1 to 10,000 μg/kg.

Routes of administration include oral, parenteral, rectal, intravaginal, topical, nasal, ophthalmic, direct injection, etc.

Changes in the viral envelope glycoproteins, in particular in the third variable (V3) region of the gp120 exterior envelope glycoprotein, determine tropism-related phenotypes (Cheng-Mayer et al., 1990; O'Brien et al., 1990; Hwang et al., Westervelt et al., 1992; Chesebro et al., 1992; Willey et al., 1994). Amino acid changes in the V3 region (Helseth et al., 1990; Freed et al., 1991; Ivanoff et al., 1991; Bergeron et al., 1992; Grimaila et al., 1992; Page et al., 1992; Travis et al., 1992) and the binding of antibodies to this domain (Putney et al., 1986; Goudsmit et al., 1988; Linsley et al., 1988; Rusche et al., 1988; Skinner et al., Javeherian et al., 1989) have been shown to disrupt a virus entry process other than CD4 binding. Accordingly, one can create derivatives and change the phenotype for a particular receptor by substituting V3 loops.

One can inhibit infection by directly blocking receptor binding. This can be accomplished by a range of different approaches. For example, antibodies. One preferred approach is the use of antibodies to the binding site for these chemokine receptors. Antibodies to these receptors can be prepared by standard means using the stable immunogenic oligomers. For example, one can use single chain antibodies to target these binding sites.

As used herein the inhibition of HIV infection means that as compared to a control situation infection is reduced, inhibited or prevented. Infection is preferably at least 20% less, more preferably at least 40% less, even more preferably at least 50% less, still more preferably at least 75% less, even more preferably at least 80% less, and yet more preferably at least 90% less than the control.

One preferred use of the antibodies is to minimize the risk of HIV transmission. These antibodies can be included in ointments, foams, creams that can be used during sex. For example, they can be administered preferably prior to or just after sexual contact such as intercourse. One preferred composition would be a vaginal foam containing one of the antibodies. Another use would be in systemic administration to block HIV-1 replication in the blood and tissues. The antibodies could also be administered in combination with other HIV treatments.

An exemplary pharmaceutical composition is a therapeutically effective amount of a the oligomer, antibody etc. that for examples affects the ability of the receptor to facilitate HIV infection or for the DNA sequence or the oligomer that can induce an immune reaction, thereby acting as a prophylactic immunogen, optionally included in a pharmaceutically-acceptable and compatible carrier. The term "pharmaceutically-acceptable and compatible carrier" as used herein, and described more fully below, includes (i) one or more compatible solid or liquid filler diluents or encapsulating substances that are suitable for administration to a human or other animal, and/or (ii) a system, such as a retroviral vector, capable of delivering the molecule to a target cell. In the present invention, the term "carriers" thus denotes an organic or inorganic ingredient, natural or synthetic, with which the molecules of the invention are combined to facilitate application. The term "therapeutically-effective amount" is that amount of the present pharmaceutical compositions which produces a desired result or exerts a desired influence on the particular condition being treated. For example, the amount necessary to raise an immune reaction to provide proplyactic protection. Typically when the composition is being used as a prophylactic immunogen at least one "boost" will be administered at a periodic internal after the initial administration. Various concentrations may be used in preparing compositions incorporating the same ingredient to provide for variations in the age of the patient to be treated, the severity of the condition, the duration of the treatment and the mode of administration.

The term "compatible", as used herein, means that the components of the pharmaceutical compositions are capable of being commingled with a small molecule, nucleic acid and/or polypeptides of the present invention, and with each other, in a manner such that does not substantially impair the desired pharmaceutical efficacy.

Dose of the pharmaceutical compositions of the invention will vary depending on the subject and upon particular route of administration used. Dosages can range from 0.1 to 100,000 μg/kg per day, more preferably 1 to 10,000 μg/kg. By way of an example only, an overall dose range of from about, for example, 1 microgram to about 300 micrograms might be used for human use. This dose can be delivered at periodic intervals based upon the composition. For example on at least two separate occasions, preferably spaced apart by about 4 weeks. Other compounds might be admisnistered daily. Pharmaceutical compositions of the present invention can also be administered to a subject according to a variety of other, well-characterized protocols. For example, certain currently accepted immunization regimens can include the following: (i) administration times are a first dose at elected date; a second dose at 1 month after first dose; and a third dose at 5 months after second dose. See Product Information, *Physician's Desk Reference*, Merck Sharp & Dohme (1990), at 1442–43. (e.g., Hepatitis B Vaccine-type protocol); (ii) Recommended administration for children is first dose at elected date (at age 6 weeks old or older); a second dose at 4–8 weeks after first dose; a third dose at 4–8 weeks after second dose; a fourth dose at 6–12 months after third dose; a fifth dose at age 4–6 years old; and additional boosters every 10 years after last dose. See Product Information, *Physician's Desk Reference*, Merck Sharp & Dohme (1990), at 879 (e.g., Diptheria, Tetanus and Pertussis-type vaccine protocols). Desired time intervals for delivery of multiple doses of a particular composition can be determined by one of ordinary skill in the art employing no more than routine experimentation.

The antibodies, DNA sequences or oligomers of the invention may also be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulfuric, nitric, phosphoric, maleic, acetic, salicylic, p-toluene-sulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acid and/or polypeptides of the invention together with one or more pharmaceutically acceptable carriers thereof and optionally any other therapeutic ingredients.

The compositions include those suitable for oral, rectal, intravaginal, topical, nasal, ophthalmic or parenteral administration, all of which may be used as routes of administration using the materials of the present invention. Other suitable routes of administration include intrathecal administration directly into spinal fluid (CSF), direct injection onto an arterial surface and intraparenchymal injection directly into targeted areas of an organ. Compositions suitable for parenteral administration are preferred. The term "parenteral" includes subcutaneous injections, intravenous, intramuscular, intrasternal injection or infusion techniques.

The compositions may conveniently be presented in unit dosage form and may be prepared by any of the methods well known in the art of pharmacy. Methods typically include the step of bringing the active ingredients of the invention into association with a carrier which constitutes one or more accessory ingredients.

Compositions of the present invention suitable for oral administration may be presented as discrete units such as capsules, cachets, tablets or lozenges, each containing a predetermined amount of the nucleic acid and/or polypeptide of the invention in liposomes or as a suspension in an aqueous liquor or non-aqueous liquid such as a syrup, an elixir, or an emulsion.

Preferred compositions suitable for parenteral administration conveniently comprise a sterile aqueous preparation of the molecule of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The term "antibodies" is meant to include monoclonal antibodies, polyclonal antibodies and antibodies prepared by recombinant nucleic acid techniques that are selectively reactive with polypeptides encoded by eukaryotic nucleotide sequences of the present invention. The term "selectively reactive" refers to those antibodies that react with one or more antigenic determinants on e.g. gp120 and do not react with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes, as well as to block bindiner interactions.

For example, cDNA clone encoding a gp120 of the present invention may be expressed in a host using standard techniques (see above; see Sambrook et al., Molecular Cloning; A Laboratory Manual, Cold Spring Harbor Press, Cold Spring Harbor, N.Y.: 1989) such that 5–20% of the total protein that can be recovered from the host is the desired protein. Recovered proteins can be electrophoresed using PAGE and the appropriate protein band can be cut out of the gel. The desired protein sample can then be eluted from the gel slice and prepared for immunization. Preferably, one would design a stable cell capable of expressing high levels of the proteins which be selected and used to generate antibodies For example, mice can be immunized twice intraperitoneally with approximately 50 micrograms of protein immunogen per mouse. Sera from such immunized mice can be tested for antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp. San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

To further improve the likelihood of producing an antibody as provided by the invention, the amino acid sequence of polypeptides encoded by a eukaryotic nucleotide sequence of the present invention may be analyzed in order to identify desired portions of amino acid sequence which may be associated with receptor binding. For example, polypeptide sequences may be subjected to computer analysis to identify such sites.

For preparation of monoclonal antibodies directed toward polypeptides encoded by a eukaryotic nucleotide sequence of the invention, any technique that provides for the production of antibody molecules by continuous cell lines may be used. For example, the hybridoma technique originally developed by Kohler and Milstein (Nature, 256: 495–497, 1973), as well as the trioma technique, the human B-cell hybridoma technique (Kozbor et al., Immunology Today, 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al. U.S. Pat. Nos. 4,704,694 and 4,976,778).

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to the resultant antibodies or to other molecules of the invention. See, for example, "Conjugate Vaccines", Contributions to Microbiology and Immunology, J. M. Cruse and R. E. Lewis, Jr (eds), Carger Press, New York, (1989), the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myasthenia Gravis by toxin-acetylcholine receptor conjugates." Jour. Immun. 133:1335–2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity". Immunological Reviews 62:185–216; and Vitetta et al., supra).

Preferred linkers are described in the literature. See, for example, Ramakrishnan, S. et al., Cancer Res. 44:201–208 (1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylaminopropyl) carbodiimide hydrochloride; (ii) SMPT (succinimidyloxycarbonyl-alpha-methyl-alpha-(2-pyridyl-dithio)-toluene (Pierce Chem. Co., Cat. (21558G); (iii) SPDP (succinimidyl-6[3-(2-pyridyldithio) propionamido] hexanoate (Pierce Chem. Co., Cat #21651G); (iv) Sulfo-LC-SPDP (sulfosuccinimidyl 6[3-(2-pyridyldithio)-propianamide] hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Antibodies of the present invention can be detected by appropriate assays, such as the direct binding assay discussed earlier and by other conventional types of immunoassays. For example, a sandwich assay can be performed in which the receptor or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide of the present invention is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid and the label bound to the solid phase is measured, the amount of the label detected serving as a measure of the amount of anti-urea transporter antibody present in the sample. These and other immunoassays can be easily performed by those of ordinary skill in the art.

The following Examples serve to illustrate the present invention, and are not intended to limit the invention in any manner.

Specific groups of HIV-1 neutralizing antibodies directed against the gp120 V3 loop or CD4-induced (CD4i) epitopes were able to block the binding of gp120-sCD4 complexes to CCR5-expressing cells (3,4). The CD4i epitopes are conserved, discontinuous gp120 structures that are exposed better after CD4 binding (5). Mutagenic analysis suggested that elements of the conserved stem of the V1V2 stem-loop and of the fourth conserved region of gp120 comprise the CD4i epitopes (5). The following examples demonstrate that conserved gp120 residues near or within the CD4i epitopes are critical for CCR5 binding.

An assay was established that could assess the CCR5-binding ability of a panel of HIV-1 gp120 glycoprotein mutants. The mutants were created by the introduction of single amino acid changes in gp120 residues near or within regions previously shown to be important for the integrity of the CD4i epitopes (5). The wtΔ glycoprotein, which lacks the V1/V2 variable loops and the N-terminus and is derived from the YU2 primary macrophage-tropic HIV-1 isolate (7), was the starting point for the studies (FIGS. 1A-E). This protein was chosen because it had been shown to bind CD4 and CCR5 with high affinity (3,8,9). Furthermore, the use of this protein minimized the opportunities for indirect effects of gp120 amino acid changes on CCR5 binding (e.g., by repositioning the V1/V2 loops, which can mask CD4i epitopes (9)). Metabolically labeled wtΔ and mutant derivatives were produced in 293T cells and incubated with mouse L1.2 cells stably expressing human CCR5 (3), in either the absence or presence of sCD4. The cells were washed and lysed, and bound gp120 protein was detected by precipitation with a mixture of sera from HIV-1 infected individuals (10).

The wtΔ protein efficiently bound to the L1.2-CCR5 cells in the presence of sCD4. Binding was dramatically reduced when sCD4 was not present in the assay. The wtΔ protein binding to the L1.2-CCR5 cells was inhibited by preincubation of the wtΔ protein with the 17b antibody. Binding was also inhibited by incubation of the L1.2-CCR5 cells with the 2D7 antibody against CCR5 (C 11) or with the CCR5 ligand, MIP-1,8 (12). The C11 antibody, which is directed against a gp120 region dispensable for CCR5 binding (3), did not block the binding of the wtΔ protein to the L1.2-CCR5 cells (data not shown). The wtΔ protein did not bind appreciably to the parental L1.2 cells not expressing CCR5 even in the presence of sCD4. These results indicate that the wtΔ protein binds CCR5 in a specific, CD4-dependent manner.

The binding of the panel of gp120 mutants to the L1.2-CCR5 cells in the absence and presence of sCD4 was measured. The recognition of the mutant proteins by sCD4 and by monoclonal antibodies that recognize discontinuous gp120 epitopes (5,13) was assessed in parallel (10). Changes in several gp120 amino acids resulted in dramatic reductions in the ability of the protein to bind to L1.2-CCR5 cells in the presence of sCD4 (Table 1). In some cases (257 T/D, 370 E/Q and 383 F/S), the attenuated CD4-binding ability of the mutant proteins could account for the observed reduction in binding to the L1.2-CCR5 cells. In most cases, however, the mutant proteins that were deficient in CCR5 binding still bound sCD4 and at least one of the monoclonal antibodies recognizing discontinuous gp120 epitopes. As expected, some of the introduced amino acid changes decreased recognition by the 17b antibody. Interestingly, two of the gp120 amino acid changes (437 P/A, 442 Q/L) resulted in an increase in CCR5 binding compared with the wtΔ protein, even though CD4 binding was not significantly increased. In the absence of sCD4, the 437 P/A and 442 Q/L envelope glycoprotein mutants bound to the L1.2-CCR5 cells slightly better than the other mutants and the wtΔ protein, which exhibited very low levels of binding (data not shown).

Table 1. Phenotypes of HIV-1 gp120 mutants. The ability of the wtΔ and mutant glycoproteins to bind CCR5 expressed on L1.2 cells was determined (10). The recognition of the wtΔ and mutant glycoproteins by sCD4 and monoclonal antibodies was determined (10). All values reported are relative to those seen for the wtΔ protein. Values represent the average of at least two independent experiments and exhibited less than 30% variation from the value shown.

| Protein (Fractional Solvent Accessibility)* | CCR5 BindingH | Ligand Binding | | | |
|---|---|---|---|---|---|
| | | sCD4 | 17b | CG10 | F105 |
| wtΔ | 1.00 | 1.00 | 1.00 | 1.00 | 1.00 |
| 107 D/R | 1.02 | 1.02 | 0.97 | 1.11 | 1.14 |
| 114 Q/L | 1.22 | 0.79 | 0.73 | 0.71 | 0.75 |
| 117 K/D (0.45) | 0.15 | 0.74 | 0.64 | 0.42 | 0.83 |
| 121 K/D (0.57) | 0.07 | 0.73 | 0.11 | 0.0 | 0.99 |
| 122 US | 0.98 | 0.84 | 1.07 | 0.18 | 1.11 |
| 123 T/D (0.49) | 0.08 | 0.99 | 1.06 | 0.0 | 1.25 |
| 197 N/D | 1.33 | 1.34 | 0.80 | 0.81 | 1.11 |
| 199 S/L | 1.50 | 1.32 | 0.94 | 1.03 | 1.04 |
| 200 V/S | 0.84 | 0.91 | 1.05 | 0.49 | 1.06 |
| 201 I/A | 0.46 | 0.90 | 0.67 | 0.84 | 0.81 |
| 203 Q/L | 0.68 | 0.85 | 0.88 | 0.52 | 0.93 |
| 207 KID (0.23) | 0.0 | 0.85 | 0.46 | 0.13 | 0.98 |
| 209 S/L | 1.00 | 1.11 | 0.85 | 1.01 | 1.00 |
| 210 F/S | 0.65 | 0.81 | 0.81 | 0.85 | 0.74 |
| 211 E/K | 0.73 | 1.13 | 1.03 | 1.12 | 1.24 |
| 257 T/D | 0.05 | 0.0 | 0.49 | 0.06 | 0.0 |
| 295 N/E | 0.86 | 0.75 | 0.73 | 0.98 | 0.79 |
| 308 N/D | 0.31 | 1.10 | 0.89 | 0.93 | 1.03 |
| 317 US | 0.08 | 1.12 | 1.05 | 1.13 | 1.03 |
| 330 H1A | 0.22 | 0.75 | 0.55 | 0.66 | 0.64 |
| AV3 (/~298–329) | 0.0 | 0.80 | 0.08 | 1.27 | 0.93 |
| 370 E/Q | 0.17 | 0.0 | 1.04 | 0.12 | 0.0 |
| 372 V/S | 0.85 | 1.03 | 1.08 | 1.09 | 0.44 |

-continued

| Protein (Fractional Solvent Accessibility)* | CCR5 BindingH | Ligand Binding | | | |
|---|---|---|---|---|---|
| | | sCD4 | 17b | CG10 | F105 |
| 373 T/D | 0.48 | 1.12 | 1.10 | 1.16 | 1.10 |
| 377 N/E (0.04) | 0.22 | 0.71 | 0.52 | 0.65 | 0.60 |
| 381 E/R (0.07) | 0.07 | 0.81 | 0.75 | 0.29 | 0.96 |
| 383 F/S | 0.04 | 0.0 | 0.0 | 0.07 | 0.0 |
| 386 N/D | 1.22 | 1.14 | 0.97 | 0.90 | 0.97 |
| 419 R/D (0.82) | 0.19 | 0.86 | 0.02 | 0.48 | 0.82 |
| 420 I/R (0.14) | 0.06 | 0.59 | 0.0 | 0.72 | 0.72 |
| 421 K/D (0.32) | 0.07 | 0.86 | 0.19 | 0.0 | 0.0 |
| 422 Q/L (0.35) | 0.07 | 0.53 | 0.0 | 0.20 | 0.55 |
| 423 I/S | 0.61 | 0.97 | 0.05 | 0.30 | 1.03 |
| 424 I/S | 0.37 | 0.25 | 0.48 | 0.83 | 0.81 |
| 426 M/A | 0.75 | 0.69 | 0.69 | 0.72 | 1.11 |
| 429 E/R | 1.54 | 1.17 | 1.00 | 1.05 | 0.82 |
| 432 K/A | 0.61 | 1.0 | 0.92 | 0.0 | 1.45 |
| 434 MIA | 1.22 | 0.90 | 0.65 | 0.07 | 1.04 |
| 435 Y/S | 0.21 | 0.33 | 0.22 | 0.29 | 1.00 |
| 436 A/S | 0.98 | 1.05 | 0.91 | 0.99 | 1.23 |
| 437 P/A | 1.79 | 0.80 | 0.68 | 0.78 | 0.82 |
| 438 P/A (0.28) | 0.06 | 1.18 | 1.00 | 1.13 | 1.18 |
| 439 I/A | 0.45 | 0.68 | 0.76 | 0.76 | 0.84 |
| 440 R/D (0.43) | 0.09 | 1.03 | 1.05 | 1.05 | 1.13 |
| 441 GN (0.91) | 0.0 | 0.67 | 0.70 | 0.62 | 0.78 |
| 442 Q/L | 2.00 | 1.11 | 0.74 | 1.05 | 0.83 |
| 444 RID (0.80) | 0.25 | 0.79 | 0.67 | 0.94 | 0.74 |
| 474 D/R | 1.03 | 0.59 | 0.81 | 0.74 | 0.0 |

*The number of the mutant wtΔ glycoproteins is based on the sequence of the prototypic HXBc2 gp120 glycoprotein (24), with 1 representing the initiator methionine. The wild-type YU2 gp120 residue is listed, followed by the substituted residue. Amino acid abbreviations: A, alanine; D, aspartic acid; E, glutamic acid; F. phenylalanine; G. glycine; H. histidine; I, isoleucine; K, Lysine; L, leucine; M, methionine; N. asparagine; P. proline; Q. glutamine; R. arginine; S. serine; T.threonine; V, valine; Y. tyrosine. The fractional solvent accessibilities associated with gp120 residues in which changes specifically disrupted CCR5 binding are shown in parentheses. Fractional solvent accessibility was calculated as the ratio of solvent-accessible surface area for atoms of amino-acid residue X in the gp120 core (without carbohydrate moieties) to the area obtained after reducing the structure to a Gly-X-Gly tripeptide (24). Values cited are for side-chain atoms exceptfor glycine 441 where the value for all atoms is given.

HThe binding of the wtΔ glycoprotein to L1.2-CCR5 cells was shown to be linearly related to the concentration of wtΔ protein in the transfected 293T cell supernatants, over the range of concentrations used in these experiments. The total amount of wtΔ and mutant glycoprotein present in the 293T cell supernatants was estimated by precipitation with an excess of a mixture of sera from HIV-1-infected individuals. The amount of wtΔ and mutant glycoprotein bound to the L1.2-CCR5 cells was determined as described (10). The value for CCR5 binding was calculated using the following formula:

$$CCR5\ \text{binding} = \frac{\text{Bound mutant protein}}{\text{Bound wt}\Delta\text{ protein}} \times \frac{\text{Total wt}\Delta\text{ protein}}{\text{Total mutant protein}}$$

The recognition of the wtΔ and mutant glycoproteins by sCD4 and antibodies was determined by precipitation of radiolabeled envelope glycoproteins in transfected 293T cell supernatants as described (10). In parallel, the labeled envelope glycoproteins were precipitated with an excess of a mixture of sera from HIV-1-infected individuals. The value for ligand binding was calculated using the following formula:

$$\text{Ligand binding} = \frac{\text{Mutant protein}_{\text{ligand}}}{\text{wt}\Delta \text{ protein}_{\text{ligand}}} \times \frac{\text{wt}\Delta \text{ protein}_{\text{serum mixture}}}{\text{Mutant protein}_{\text{serum mixture}}}$$

In the sCD4 and 17b columns, the values in bold indicate gp120 residues that exhibit decreased solvent accessibility in the presence of the two-domain sCD4 or 17b Fab, respectively, in the ternary complex (6). Changes in solvent accessibility were calculated using the MS program of Michael Connolly.

Graphics. Molecular graphics were produced using Midas-Plus (University of California, San Francisco) and GRASP.30

Assignment of variability. Variability in gp120 residues was assessed using an alignment of sequences derived from approximately 400 HIV-1, HIV-2 and simian immunodeficiency viruses.[13] Residues were assigned variability indices and color coded as follows:

Red: conserved in all primate immunodeficiency viruses;

Orange: conserved in all HIV-1, including groups M and 0 and chimpanzee isolates;

Yellow: some variation among HIV-1 isolates (divergence from the consensus sequence in 1–8 of the 12 HIV-1 groups examined).

Green: variable among HIV-1 isolates (divergence from the consensus sequence in. 9 of the 12 HIV-1 groups examined).

Molecular modeling. Residues 88, 89, and 397–409, which are disordered in the ternary complex crystals (H. Deng et al., *Nature,* 381:661–666 (1996), were built manually using the program TOM. For the V4 loop (residues 397–409), a dominant constraint was the distance between the ordered residues 396 and 410 (C—C distance of 26.88 Δ). For the carbohydrate, examination of the N-linked carbohydrate in several crystal structures (e.g. 1fc2, 1gly, 1lte) showed that the core common to both high-mannose and complex N-linked sugars, $(NAG)_2(MAN)_3$, did not differ greatly in conformation after alignment of the first NAG. This core, which represents roughly half the total glycosylation for a typical N-linked site, was built onto each of the 18 consensus N-linked glycosylation sites found on the HXBc2 gp120 core. The stereochemistry of this initial model was refined using 4; simulated annealing in XPLOR. Briefly, the model was heated to between 2,500' and 3,500° K., and "slow cooled" in steps of 25° to 300° K. At each step, molecular dynamics were performed with the core gp120 fixed, allowing only the modeled residues and carbohydrate (including any attached Asn) to move. In three separate runs, performing molecular dynamics for 5 fs/step, all steric clashes could be removed and the geometry idealized, with an average root mean square (RMS) of carbohydrate movement of only ~3.5Δ. Four subsequent runs were made using dynamic times of between 50–75 fs/step. The carbohydrate positions obtained from these runs differed more substantially from those in the starting model (average carbohydrate RMS difference of roughly 8Δ). Two of the models from these longer annealings were much more similar to each other than to the rest (RMS differences in carbohydrate of ~4Δ versus ~8Δ for all other models). One had been heated to 3,500° K. with dynamics of 75 fs/step. The other (shown in the figures here) was heated to only 2,500° K. with dynamics of 50 fs/step. In general the RMS movement of the NAG sugars was roughly half the RMS movement of the MAN sugars, reflecting greater conformational flexibility further from the protein surface.

In primary sequence, human and simian immunodeficiency virus gp120 glycoproteins consist of five variable regions (V1–V5) interposed among more conserved regions (G. Alkhatib et al., *Science* 272:1955–1958 (1996)). Variable regions V1–V4 form, exposed loops anchored at their bases by disulfide bonds (L. Wu et al., *Nature,* 384:179–183 (1996)). Neutralizing antibodies recognize both variable and conserved gp120 structures. The V2 and V3 loops contain epitopes for strain-restricted neutralizing antibodies (E. Emini et al., *Nature,* 355:728–730 (1992); S. Putney et al., *Science,* 234:1392–1395 (1986); and C. Bruck et al., *Colloque des Cent Garde,* 227–233 (1990). More broadly neutralizing antibodies recognize discontinuous, conserved epitopes in three regions of the gp120 glycoprotein (Table 2). In HIV-1-infected humans, the most abundant of these are directed against the CD4 binding site (CD4BS) and block gp120 CD4 interaction (Y. Feng et al., *Science* 272: 872–877 (1996); and H. Choe et al., *Cell,* 85:1135–1148 (1996)). Less common are antibodies against epitopes induced or exposed upon CD4 binding (CD4i) (P. Berman et al., *Nature,* 345:622–625 (1990)). Both CD4i and V3 antibodies disrupt the binding of gp120-CD4 complexes to chemokine receptors (B. Doranz et al., *Cell,* 85:1149–1158 (1996); and T. Draoic et al., *Nature,* 381:667–673 (1996)). A third gp120 neutralization epitope is defined by a unique monoclonal antibody, 2G 12, (W. Robey et al., *Proc. Natl. Acad. Sci. U.S.A.,* 83:7023–7027 (1986)) which does not efficiently block receptor binding T. Draoic et al., *Nature,* 381:667–673 (1996)).

The X-ray crystal structure of an HIV-1 gp120 core in a ternary complex with two-domain soluble CD4 and the Fab fragment of the CD4i antibody, 17b. The gp120 core lacks the V1/V2 and V3 variable loops, as well as N- and C-terminal sequences, which interact with the gp41 glycoprotein (M. Lu et al., *Nature Structural Biol.,* 2:1075–1082 (1995)), and is enzymatically deglycosylated (H. Deng et al., *Nature,* 381:661–666 (1996); and K. Steimer et al., *Science,* 254:105–108 (1991)). Despite these modifications, the gp120 core binds CD4 and antibodies against CD4BS and CD4i epitopes (K. Steimer et al., *Science,* 254:105–108 (1991); and M. Posner et al., *J. Immunol.,* 146:4325–4332 (1991)) and thus retains structural integrity. The gp120 core is composed of an inner domain, an outer domain and a third element, the "bridging sheet" (H. Deng et al., *Nature,* 381:661– 666 (1996)) (FIG. 1*a*). All three structural elements contribute, either directly or indirectly, to CD4 and chemokine receptor binding.[12]

Although generally well-conserved compared with the five variable regions, some variability in the surface of the gp120 core is evident when the sequences of all primate immunodeficiency viruses are analyzed. This variability is disproportionately associated with the surface of the outer domain proximal to the V4 and V5 regions and removed from the receptor-binding regions (FIGS. 1C and 2). The A, C, D and E surface loops (12) contribute to the variability of this surface. The potential N-linked glycosylation sites present in the gp120 core are concentrated in this variable half of the protein. In fact, the only conserved residues apparent on this relatively variable surface are asparagine 356 and threonine/serine 358, which constitute a complex carbohydrate addition site within the E loop. Since most carbohydrate moieties may appear as "self" to the immune system, the extensive glycosylation of the outer domain surface should render it less visible to immune surveillance.

This helps to explain why antibodies directed against this gp120 surface have been identified so infrequently.

Figure 2:
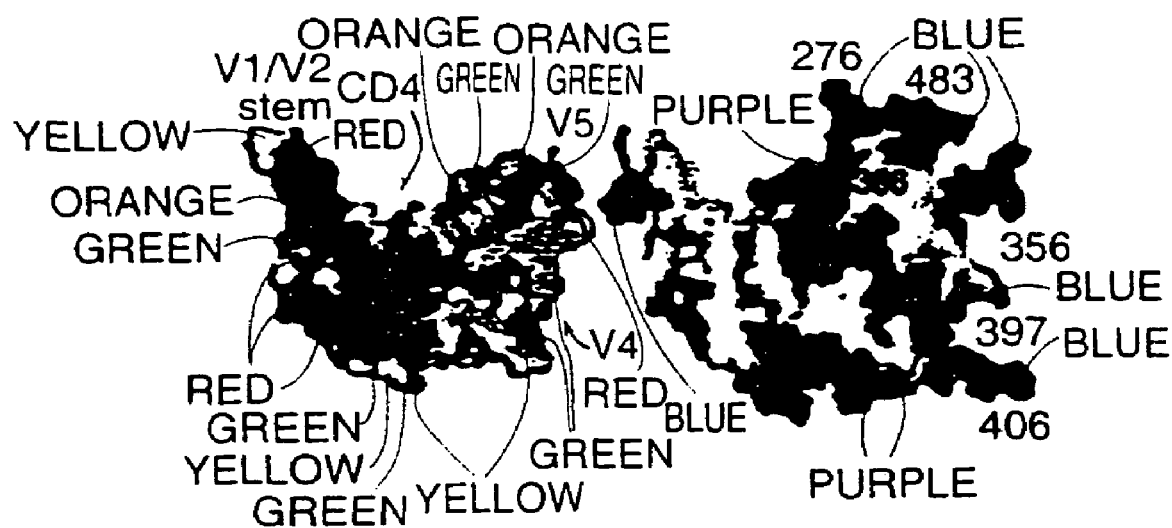
FIG. 2 shows the molecular surface of the gp120 outer domain colored according to the variability observed in gp120 residues among primate immunodeficiency viruses. Red indicates residues conserved among all primate immunodeficiency viruses; orange, residues conserved in all HIV-1 isolates; yellow, residues exhibiting some variation among HIV-1 isolates; and green, residues exhibiting significant variability among HIV-1 isolates. The inner gp120 domain is colored red and the outer domain is colored yellow. The Bridging sheet" is colored orange. The N- and C-termini of the truncated gp120 core are labeled, as are the positions of structures related to the gp120 variable regions, V1–V5. The HA, TIC, ED and HE surface loops 2 are shown. The position of the "Phe 43" cavity involved in CD4 binding is indicated by an asterisk. A gp120 surface implicated in binding to the CCR5 chemokine receptor is indicated. The variability of the gp120 surface shown is underestimated since the V4 variable loop, which is not resolved in the structure, contributes to this surface (approximate location is indicated). The position of the V5 region is shown. Also note the highly conserved glycosylation site (asparagine 356 and threonine/serine 358) within the HE loop, between the V5 and V4 regions. In the figure on the right, the V4 loop and the carbohydrates are modeled, as described in Materials and Methods. The complex carbohydrate addition sites used in mammalian cells 4 are colored light blue, and the high-mannose sites are colored dark blue. The gp120 protein surface is shown in white.
Figure 3A:
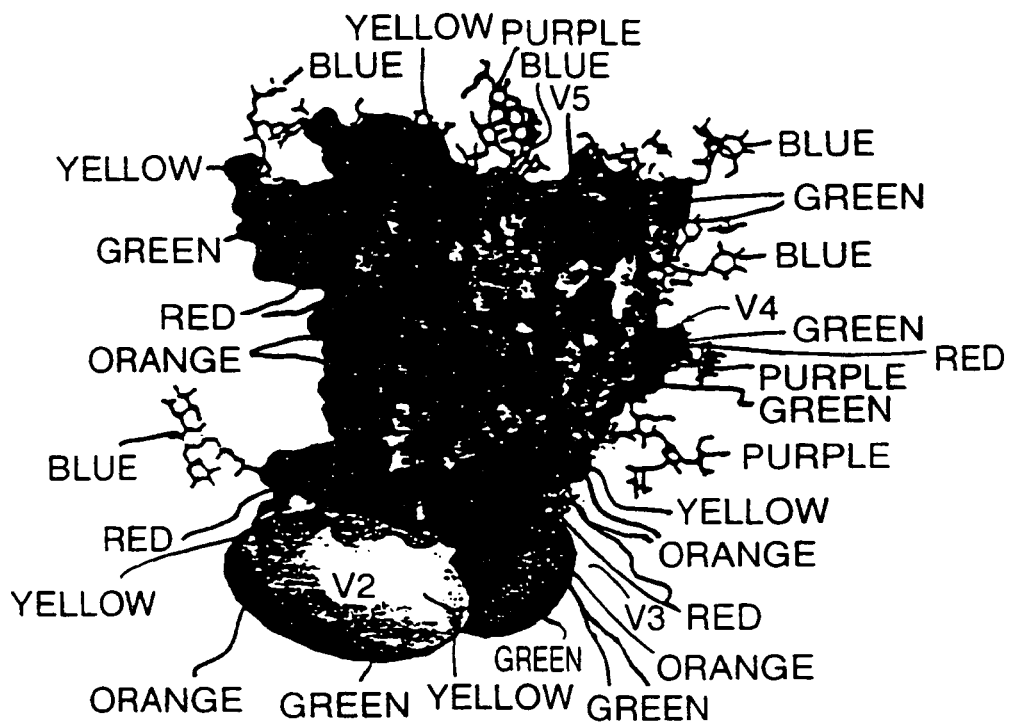
FIGS. 3A–3D show the spatial relationship of epitopes on the HIV-1 gp120 glycoprotein.
Figure 3B:
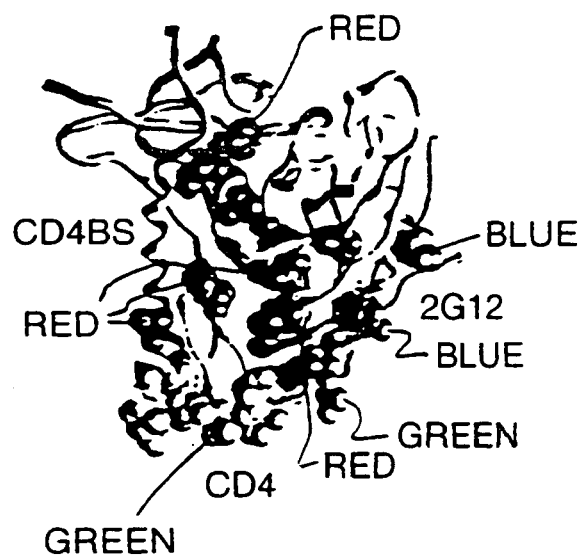
Figure 3C:
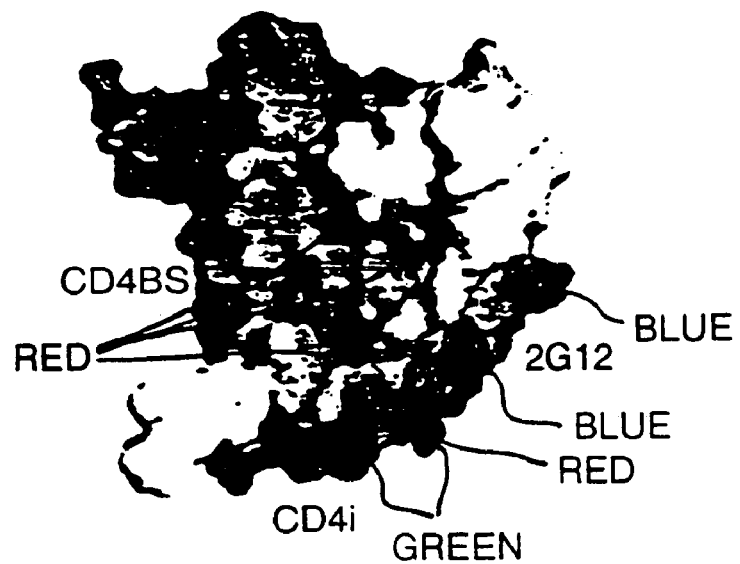

The receptor-binding regions retained in the gp120 core are well-conserved among primate immunodeficiency viruses (H. Deng et al., *Nature,* 381:661–666 (1996)). Also highly conserved is the surface of the inner domain spanned by the β1 helix and located opposite the variable surface described above. This surface is likely to interact with gp41 and/or with N-terminal gp120 segments absent from the gp120 core. This inner domain surface and the receptor-binding regions are devoid of glycosylation. In conjunction with prior mutagenic and antibody competition analyses, (A. Pinter et al., *J. Virol.,* 63:2674–2679 (1989); M. Lu et al., *Nature Structural Biol.,* 2:1075–1082 (1995); P. Berman et al., *Nature,* 345:622–625 (1990); W. Robey et al., *Proc. Natl. Acad. Sci. U.S.A.,* 83:7023–7027 (1986); J. Rusche et al., *Proc Natl. Acad. Sci. U.S.A.,* 85:3198–3202 (1988); and K. Steimer et al., *Science,* 254:105–108 (1991)) the gp120 core structure reveals for the first time the spatial positioning of the conserved gp120 neutralization epitopes. Although the major variable loops are either absent (V1/V2 and V3) or poorly resolved (V4) in the gp120 core structure, their approximate positions can be deduced (FIG. 3A). The conserved gp120 neutralization epitopes are discussed in relation to these variable loops and to the variable, glycosylated core surface.

a) CD4i epitopes. The gp120 epitope recognized by the CD4i antibody, 17b, can be directly visualized in the crystallized ternary complex (FIGS. 3B and 3C). Strands from the gp120 fourth conserved (C4) region and the V1/V2 stem contribute to an antiparallel β-sheet (the "bridging sheet" (see FIG. 1A)) that contacts the antibody. The vast majority of gp120 residues previously implicated in formation of the CD4i epitopes[18] (Table 2) are located either within this β-sheet or in nearby structures. With the exception of Thr 202 and Met 434, the gp120 residues in contact with the 17b Fab are highly conserved among HIV-1 isolates (FIG. 1C, 2 and 3A). The prominent ("male") CDR3 loop of the 17b heavy chain dominates the contacts with gp120, with additional contacts through the heavy chain CDR2 (H. Deng et al., *Nature,* 381:661–666 (1996)). Unusually, there are minimal 17b light chain contacts, leaving a large gap between the gp120 core and most of the 17b light chain surface. In the complete gp120 glycoprotein, this gap is likely occupied by the V3 loop. This is consistent with the position and orientation of the V3 stem on the gp120 core structure (H. Deng et al. *Nature,* 381:661–666 (1996)), the effect of V3 deletions on the binding of CD4i antibodies in the absence of soluble CD4 (M. Posner et al., *J. Immunol.,* 146:4325–4332 (1991)), the competition of some V3-directed antibodies with CD4i antibodies A. Pinter et al., *J. Virol.,* 63:2674–2679 (1989)), and the ability of both antibody groups to block chemokine receptor binding (B. Doranz et al., *Cell,* 85:1149–1158 (1996); and T. Draoic et al., *Nature,* 381:667–673 (1996). The chemokine receptor-binding region of gp120 likely consists of elements near or within the "bridging sheet" and the V3 loop.

The V2 loop likely resides on the side of the 17b epitope opposite the V3 loop (FIG. 3A). The V1/V2 loops, which vary from 57 to 86 residues in length,[13] are dispensable for HIV-1 replication (M. Posner et al., *J. Immunol.,* 146:4325–4332 (1991)); and R. Wyatt et al., *J. Virol.,* 69:5723–5733 (1995)) but decrease the sensitivity of viruses to neutralization by antibodies against V3 and CD4i epitopes (R. Wyatt et al., *J. Virol.,* 69:5723–5733 (1995)). The latter effect is mediated primarily by the V2 loop, (M. Posner et al., *J. Immunol.,* 146:4325–4332 (1991)) suggesting that part of the V2 loop folds back along the V1/V2 stem to mask the "bridging sheet" and adjacent V3 loop. The proximity of the V2 and V3 loops is supported by the observation that, in monkeys infected with simian-human immunodeficiency viruses (SHIVs), neutralizing antibodies are raised against discontinuous epitopes with V2 and V3 components (B. Etemad-Moghadam and J. Sodroski). The CD4i epitopes are apparently masked by the flanking V2 and V3 loops, requiring the evolution of antibodies with protruding ("male") CDRs to access these conserved epitopes. CD4 binding has been suggested to reposition the V1/V2 loops, thus exposing the CD4i epitopes (M. Posner et al., *J. Immunol.,* 146: 4325–4332 (1991)). The presence of contacts between the V1/V2 stem and CD4 in the crystal structured is consistent with this model.

b) CD4BS epitopes. CD4 makes a number of contacts within a recessed pocket on the gp120 surface. The gp120-CD4 interface includes two cavities, one water-filled and bounded equally by both proteins, the other extending into the gp120 interior and contacting CD4 only at phenylalanine 43 (H. Deng et al., *Nature,* 381:661–666 (1996)). Tables 1, 2 and FIGS. 3B and 3C show the gp120 residues implicated in the formation of CD4BS epitopes recognized by eight representative antibodies. CD4BS epitopes are uniformly disrupted by changes in Asp 368 and Glu 370, (J. Rusche et al., *Proc. Natl. Acad. Sci. U.S.A.,* 85:3198–3202 (1988)) which surround the opening of the "Phe 43 cavity". These residues are located on a ridge at the intersection of the two receptor-binding gp120 surfaces, consistent with competition studies suggesting that CD4BS epitopes overlap both the CD4i epitopes and the binding site for CD4 (A. Pinter et al., *J. Virol.,* 63:2674–2679 (1989); and P. Berman et al., *Nature,* 345:622–625 (1990)). The location of the gp120 residues implicated in the formation of the CD4BS epitopes suggests that important elements of the CD4-binding surface of gp120 are accessible to antibodies.

Some CD4BS antibodies, like IgG1b12, are particularly potent at neutralizing HIV-1 (J. Robinson et al., *AIDS Res. Hum. Retro,* 6:567–580 (1990)). IgG1b12 binding is disrupted by gp120 changes that affect the binding of other CD4BS antibodies but, atypically, is sensitive to changes in the V1/V2 stem-loop structured The observation that some well-conserved residues in the gp120 V1/V2 stem contact CD4 (H. Deng et al., *Nature,* 381:661–666 (1996)) raises the possibility that this protruding structure also contributes to the IgG1b12 epitope. This might increase the ability of the antibody to access the assembled envelope glycoprotein trimer, thus increasing neutralizing capability.

While the CD4BS epitopes and the CD4-binding site overlap, several observations demonstrate that the binding of CD4BS antibodies differs from that of CD4. Changes in Trp 427, a gp120 residue that contacts both the "Phe 43 cavity" and CD4, uniformly disrupt CD4 binding but affect the binding of only some CD4BS antibodies (Table 2). Conversely, some changes in other cavity-lining gp120 residues, Ser 256 and Thr 257, affect the binding of CD4BS antibodies more than the binding of CD4 (J. Rusche et al., *Proc. Natl. Acad. Sci U.S.A.,* 85:3198–3202 (1988)). Since the recessed position of Ser 256 and Thr 257 in the current crystal structure (FIGS. 3B and 3C) makes direct contacts with antibody unlikely, either the effects of changes in these residues are indirect or the CD4BS antibodies recognize a gp120 conformation that differs from the CD4-bound state. With respect to the latter possibility, several of the residues implicated in the integrity of the CD4BS epitopes are located in the interface between the inner and outer gp120 domains. CD4BS antibodies might recognize a gp120 conformation in which the spatial relationship between the domains is altered compared with the CD4-bound state, thus allowing better surface exposure of these residues. Differences between the CD4BS epitopes and the CD4-binding site create opportunities for neutralization escape (J. Rusche et al., *Proc. Natl. Acad. Sci. U.S.A.*, 85:3198–3202 (1988)). The gp120 residues surrounding the "Phe 43" cavity are highly conserved among primate immunodeficiency viruses (FIG. 3A), but the observed modest variation in adjacent surface-accessible residues (e.g., Pro 369, Thr 373 and Lys 432) could account for decreased recognition of the gp120 glycoprotein from some geographic clades of HIV-1 by CD4BS antibodies (S. Tilley et al., *Res. Virol.*, 142:247–259 (1991)). Additional potential for variation near or within the CD4BS epitopes is created by the unusual water-filled cavity in the gp120-CD4 binding interface, since CD4 binding can apparently tolerate change in the gp120 residues contacting this cavity (H. Deng et al., *Nature*, 381:661–666 (1996)).

The recessed nature of the CD4 binding pocket on gp120 (FIG. 1B) can delay the generation of high-affinity antibodies against the CD4BS epitopes and may afford opportunities to minimize the antviral efficacy of such antibodies once they are elicited. The degree of recession is probably much greater on the full-length, glycosylated gp120 than is evident on the crystallized gp120 core. The recessed pocket is flanked on one side by the V1/V2 stem-loop structure. The characterization of HIV-1 escape mutants from the IgG1b12 CD4BS antibody and the mapping of several V2 conformational epitopes support a model in which the V2 loop folds back along the V1/V2 stem, with V2 residues 183–188 proximal to Asp 368 and Glu 370. This model is consistent with observations that V1/V2 changes, in combination with V3 changes, can alter the exposure of the adjacent CD4BS epitopes, particularly on the assembled trimer (R. Wyatt et al., *J. Virol.*, 67:4557–4565 (1993)). The high temperature factors associated with the V1/V2 stems imply flexibility in this protruding element, expanding the potential range of space occupied by the V1/V2 stem-loop structure. This could enhance masking of the adjacent CD4BS and CD4i gp120 epitopes and divert antibody responses towards the variable loops.

Glycosylation can modify the interaction of antibodies with CD4BS epitopes. The D loop, on the rim of the CD4-binding pocket opposite the V1/V2 stem, contains a well-conserved glycosylation site, asparagine 276. Changes in this site and at the adjacent alanine 281 have been associated with escape from the neutralizing activity of patient sera (D. Ho et al., *J. Virol.*, 65:489–493 (1991)) and have been seen in SHIVs extensively passaged in monkeys (M. Thali et al., *J. Virol.*, 67:39783988 (1993)). Another conserved glycosylation site at asparagine 386 lies adjacent to both CD4BS and CD4i epitopes (FIG. 1D) and could diminish antibody responses against those sites. Additionally, in various HIV-1 strains, carbohydrates are added to the V2 loop segment (residues 186–188) thought to be proximal to the CD4BS epitopes.

c) The 2G12 epitope. The integrity of the 2G12 epitope is disrupted by changes in gp120 glycosylation, either by glycosidase treatment or mutagenic alteration of specific N-linked carbohydrate addition sites (W. Robey et al., *Proc. Natl. Acad. Sci. U.S.A.*, 83:7023–7027 (1986)). These sites are located on the relatively variable surface of the gp120 outer domain, opposite to and approximately 25 Δ away from the CD4 binding site (FIGS. 1E, 3B and 3C). The gp120 glycoprotein synthesized in mammalian cells exhibits a dense concentration of high-mannose sugars in this region (FIG. 3A). Even in the enzymatically deglycosylated gp120 core, carbohydrate residues constitute much of this surface. 2G12 likely binds at least in part to these carbohydrates, explaining the surprising conservation of the 2G12 epitope despite the variability of the underlying protein surface, which includes the stem of the V3 loop and the V4 variable region. The inclusion of carbohydrate in the epitope might also explain the apparent rarity with which these antibodies are generated. The localization of the 2G12 epitope is consistent with previous studies indicating that 2G12 forms a unique competition group (A. Pinter et al., *J. Virol.*, 63:2674–2679 (1989); and W. Robey et al., *Proc. Natl. Acad. Sci. U.S.A.*, 83:7023–7027 (1986)) and does not interfere with the binding of monomeric gp120 to either CD4 or chemokine receptors (T. Draoic et al., *Nature*, 381:667–673 (1996)). Since the 2G 12 epitope is predicted to be oriented towards the target cell upon CD4 binding (see below), the antibody may sterically impair interactions of the oligomeric envelope glycoprotein complex with host cell moieties.

Figure 4:
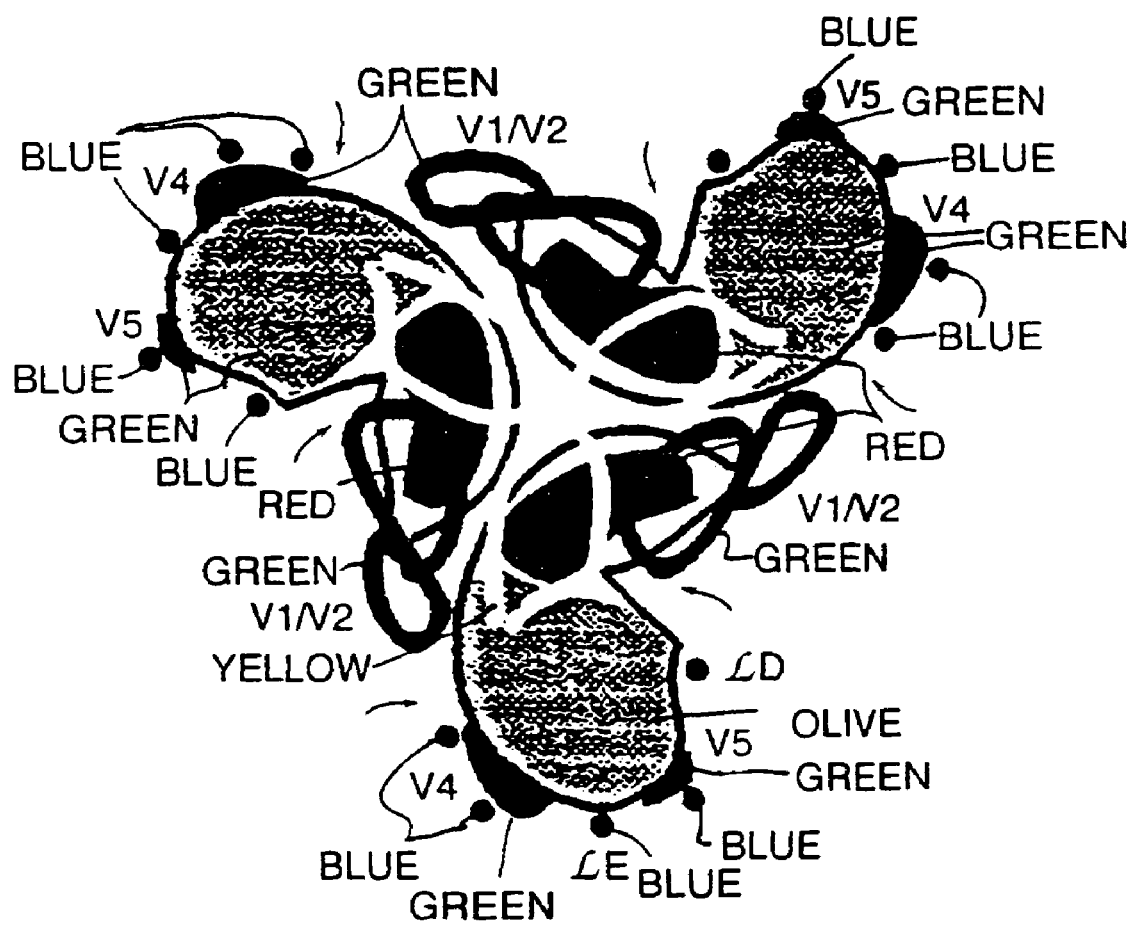
FIG. 4 is a schematic showing the probably arrangement of the HIV-1 gp120 glycoproteins in a trimeric complex. The gp120 core was organized into a trimeric array, based on the criteria discussed in the text. The perspective is from the target cell membrane, similar to that shown in FIG. 2. The CD4 binding pockets are indicated by black arrows, and the conserved chemokine receptor-binding regions are colored red. The areas shaded light green indicate the more variable, glycosylated surfaces of the gp120 cores. The approximate locations of the 2G12 epitopes are indicated by blue arrows. The approximate locations for the V3 loops (yellow) and V4 regions (green) are shown. The positions of the V5 regions (green) and some complex carbohydrate addition sites (asparagines 276, 463, 356, 397 and 406) (blue dots) are shown. The approximate locations of the large V1/V2 loops, centered on the known positions of the V1/V2 stems, are indicated (green). On one of the gp120 subunits, the positions of the ID and HE loops are indicated. The distance

Possible orientations of the exterior glycoproteins in the trimer are significantly constrained by the requirement that observed and deduced binding sites for receptors and neutralizing antibodies, sites of N-linked glycosylation, and variable structures be exposed on the surface of the assembled complex. The two-domain CD4 in the ternary complex structure was aligned to the structure of four-domain CD429 to orient the trimer model with respect to the target cell membrane. The consequences of such a model, which is shown in FIG. 4, are: a) the chemokine receptor-binding sites are clustered at the vertex of the trimer predicted to be closest to the target cell; b) both variable and conserved neutralization epitopes are concentrated on the half of gp120 facing the target cell; c) possibilities for intersubunit interactions among the variable structures that could help mask conserved neutralization epitopes are created; d) the subset of gp120 glycosylation sites to which complex carbohydrates are added in mammalian cells (L. Wu et al., *Nature*, 384:179–183 (1996)) is well-exposed on the outer periphery of the trimer; e) the highly conserved surface near the β1 helix is available for gp41 and/or gp120 protein interactions within the trimers; and f) the surface of the assembled envelope glycoprotein complex is roughly hemispherical, thus minimizing the surface area of the viral spike that is potentially exposed to antibodies.

Figure 3D:
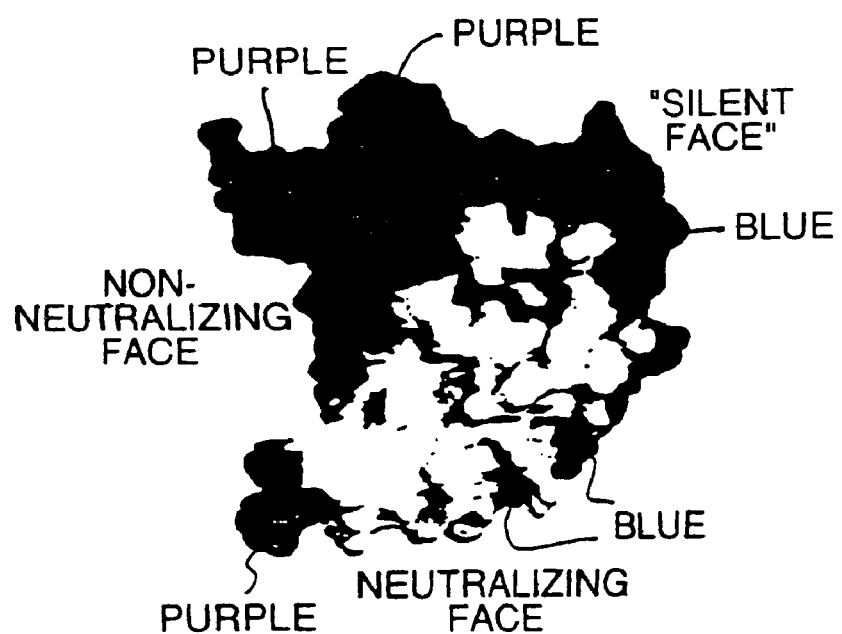

In summary, the X-ray crystal structure of the gp120 core/two-domain CD4/17b Fab complex provides a framework for visualizing key interactions between HIV-1 and the humoral immune system. Previous antibody competition analyses suggested that the gp120 surface buried in the assembled trimer elicits non-neutralizing antibodies. By contrast, the binding sites for neutralizing antibodies cluster on a different gp120 surface. Our structural studies disclose the existence of non-neutralizing and neutralizing faces of gp120, and reveal another, immunologically "silent" face of the glycoprotein (FIG. 3D). This outer domain surface, along with the major variable loops, contributes to the large fraction of the gp120 surface that is protected against antibody responses by a dense array of carbohydrates and by the capacity for variation. The conserved receptor-binding regions of gp120 represent attractive targets for immune intervention. However, the elicitation of antibodies against these conformation-dependent structures has proven inefficient. Since the gp120 epitopes near the receptor-binding regions span the inner and outer domains, in terdomain conformational shifts may decrease their representation in the immunogen pool. The recessed nature of the CD4-binding site likely contributes to its poor immunogenicity.

The sequential recognition of two receptors by primate immunodeficiency viruses allows the conserved elements of the chemokine receptor-binding site to be created or exposed by the modified polypeptides described herein.

TABLE 2

Conserved Epitopes for Neutralizing Antibodies Identified on the gp120 Core

| Competition Group | Examples of Monoclonal Antibodies | gp120 Amino Acids[b] | Probable Mechanism of Virus Neutralization | Characteristics | Selected References |
|---|---|---|---|---|---|
| CD4-Binding Site (CD4BS) | F105 15e 21h 1125h 448D 39.3 IgG1b12 830D | Asn88 (13), Asp113 (50), Lys117 (25), Ser256 (75), Thr257 (75), Asn262 (63), Ala266 (13), Asp368 (100), Glu370 (100), Tyr384 (13), Lys421 (50), Trp427 (25), Asp457 (13), Pro470 (25), Asp474 (13), Met475 (13), Asp477 (63), Asp/Leu/Tyr 482/483/484 (25) | Interference with gp120-CD4 binding | CD4BS antibodies complete with CD4 and with antibodies against CD4i epitopes | Y. Feng et al., Science, 272:872–877 (1996); H. Choe et al., Cell, 85:1149–1158 (1996); J. Rusche et al., Proc. Natl. Acad. Sci. USA, 85:3198–3202 (1988) |
| CD4-induced Epitopes (CD4i) | 17b 48d | Asn88, Lys117, Lys121, Lys207, Ser256, Thr257, Asn262, ΔV3, Glu370, Glu381, Phe382, Arg419, Ile420, Lys421, Gln422, Ile423, Trp427, Tyr435, Pro438, Met475 | Interference with chemokine receptor binding | CD4 binding increases exposure of the epitopes as a result of movement of the V2 variable loop | P. Berman et al., Nature, 345:622–625 (1990) |
| 2G12 | 2G12 | Asn295, Thr297, Ser334, Asn386, Asn392, Asn397 | Unknown | Antibody binding is dependent upon proper N-linked glycosyla-tion | W. Robey et al., Proc. Natl. Acad. Sci. USA, 83:7023–7027 (1986) |

[a]The gp120 competition groups are defined as in Reference 5.
[b]The gp120 amino acids are numbered according to the sequence of the HXBc2 (IIIB) gp120 glycoprotein, where residue 1 is the methionine at the amino-terminus of the signal peptide. Changes in the amino acids listed resulted in significant reduction in antibody binding to the gp120 glycoprotein (Ref. 18-20). The numbers in parentheses indicate the percentage of the CD4BS antibodies examined whose binding is decreased by changes in the indicated residue.

REFERENCES

1. J. Allen et al., Science, 228:1091–1094 (1983).
2. A. Daigleish et al., Nature, 312:763–767 (1984).
3. D. Klatzmann et al., Nature, 312:767–768 (1984).
4. Y. Feng et al., Science, 272:872–877 (1996).
5. J. Moore et al., J. Virol., 70:1863–1872 (1996).
6. R. Wyatt et al., J. Virol., 71:9722–9731 (1997).
7. Q. Sattentau et al., J. EXP. Med., 182:185–196 (1995).
8. M. Posner et al., J. Immunol., 146:4325–4332 (1991).
9. D. Ho et al., J. Virol., 65:489–493 (1991).
10. L. Wu et al., Nature, 384:179–183 (1996).
11. A. Trkola et se., Nature, 384:184–187 (1996).
12. P. Kwong et al., Nature, submitted.
13. G. Myers et al., Human retroviruses and AIDS. A compilation and analysis of nucleic acid and amino acid sequences. Los Alamos National Laboratory. Los Alamos, N.M. 1996.
14. C. Leonard et al., J. Biol. Chem., 265:10373–10382 (1990).
15. M. Fung et al., J. Virol., 66:848–856 (1992).
16. S. Putney et al., Science, 234:1392-1395 (1986).
17. J. Rusche et al. Proc. Natl. Acad. Sci. USA, 85:3198–3202 (1988).
18. M. Thali et al., J. Virol., 67:3978–3988 (1993).
19. A. Trkola et al., J. Virol., 70:1100-1108 (1996).
20. M. Thali et al., J. Virol., 66:56355641 (1992).
21. J. Binley et al., AIDS Res. Hum. Retroviruses, 14:191–198 (1997).
22. R. Wyatt et al., J. Virol., 69:5723–5733 (1995).
23. P. Roben et al., J. Virol., 68:4821–4828(1994).
24. J. Moore et al., J. Virol., 68:8350–8364 (1994).
25. B. Watkins et al., J. Virol., 67:7493 (1993).
26. G. Karlsson et al., J. Virol., 71:4218 (1997).
27. J. Cao et al., J. Virol., 71:9808–9812 (1997).
28. R. Wyatt et al. J. Virol., 4557–4565 (1993).
29. H. Wu et al., Nature, 387:527–530 (1997).
30. A. Nicholls et al., Proteins, 11:281–296 (1991).

All references described herein are incorporated herein by reference.

We claim:

1. A modified gp120 polypeptide comprising portions of at least two conserved regions of an envelope protein selected from a the group of lentiviruses consisting of HV-1, HIV-2 and SIV, wherein at least one of the following changes relative to the wild-type gp120 protein is made:
   (a) introduction of disulfide bonds to decrease the free energy of folding relative to the wild type gp120 protein;
   (b) filling a cavity of the gp120 protein with hydrophobic amino acid residues; or
   (c) introducing a Pro residue at a defined turn structure; wherein the modified polypeptide maintains the overall 3-dimensional structure of a discontinuous conserved epitope of the wild-type gp120, wherein the discontinuous conserved epitope is a CD4BS epitope, CD4i epitope or 2G12 epitope.

2. The modified gp120 polypeptide of claim 1, wherein the discontinuous conserved epitope is a CD4BS epitope or CD4i epitope.

3. The modified gp120 polypeptide of claim 1, wherein the gp120 protein is HIV-1.

4. The modified gp120 polypeptide of claim 3, wherein disulfide bonds are introduced between at least one of the groups of amino acids that correspond to Pro118-Ala443, Leu122-Gly431, Phe210-Gly30, or Ser256-Phe376 of the HIV-1 HXBc2 strain.

5. The modified gp120 polypeptide of claims 3 or 4, wherein at least one amino acid residue corresponding to wild-type gp120 Ser375, Val255, Arg273, Ser481, Ser447, Asn377 of the HIV-1HXBc2 strain, Thr283, or Asp477 of the HIV-1 HXBc2 strain, has been substituted with a hydrophobic amino acid residue.

6. The modified gp120 polypeptide of claim 5, wherein at least one of the following amino acid substitutions is present:
Trp for Ser375, Val255 or Arg 273;
Phe for Ser481;
Ile for Ser447 or Thr283;
Or Leu for Asn377 or Thr283.

7. The modified gp120 polypeptide of claim 5, wherein a Pro residue has been introduced at a defined turn structure.

8. The modified gp120 polypeptide of claim 4, wherein a Pro residue has been introduced at a defined turn structure.

9. The modified gp120 polypeptide of claim 3, wherein a Pro residue has been introduced at a defined turn structure.

10. The modified gp120 polypeptide of claim 7, wherein a Pro residue has been substituted for Ile423.

11. The modified gp120 polypeptide of claim 8, wherein a Pro residue has been substituted for Ile423.

12. The modified gp120 polypeptide of claim 9, wherein Pro has been substituted for Ile423.

13. The modified gp120 polypeptide of claim 1, wherein at least two of the changes have been made.

14. The modified gp120 polypeptide of claim 1, wherein at least three of the changes have been made.

15. The modified gp120 polypeptide of claim 1 wherein the cavity of the gp120 protein corresponds to Phe43 of the wild type HIV-1, HXBc2 strain.

* * * * *